US011091808B2

(12) United States Patent
Stern et al.

(10) Patent No.: US 11,091,808 B2
(45) Date of Patent: *Aug. 17, 2021

(54) METHODS FOR DETECTING INACTIVATION OF THE HOMOLOGOUS RECOMBINATION PATHWAY (BRCA1/2) IN HUMAN TUMORS

(71) Applicants: Institut Curie, Paris (FR); INSERM (Institut National de la Sante et de la Recherche Medicale), Paris (FR)

(72) Inventors: Marc-Henri Stern, Paris (FR); Elodie Manie, Paris (FR); Tatiana Popova, La Varenne Saint Hilaire (FR)

(73) Assignees: INSTITUT CURIE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 780 days.

This patent is subject to a terminal disclaimer.

(21) Appl. No.: 14/402,254

(22) PCT Filed: Jun. 6, 2013

(86) PCT No.: PCT/EP2013/061707
§ 371 (c)(1),
(2) Date: Mar. 25, 2015

(87) PCT Pub. No.: WO2013/182645
PCT Pub. Date: Dec. 12, 2013

(65) Prior Publication Data
US 2015/0140122 A1  May 21, 2015

(30) Foreign Application Priority Data

Jun. 7, 2012  (EP) .................... 12305648

(51) Int. Cl.
| | |
|---|---|
| *C12Q 1/6886* | (2018.01) |
| *C12Q 1/6827* | (2018.01) |
| *A61K 31/131* | (2006.01) |
| *A61K 31/166* | (2006.01) |
| *A61K 31/282* | (2006.01) |
| *A61K 31/407* | (2006.01) |
| *A61K 31/454* | (2006.01) |
| *A61K 31/502* | (2006.01) |
| *A61K 31/5025* | (2006.01) |
| *A61K 31/55* | (2006.01) |
| *A61K 33/243* | (2019.01) |
| *A61K 33/24* | (2019.01) |

(52) U.S. Cl.
CPC .......... *C12Q 1/6886* (2013.01); *A61K 31/131* (2013.01); *A61K 31/166* (2013.01); *A61K 31/282* (2013.01); *A61K 31/407* (2013.01); *A61K 31/454* (2013.01); *A61K 31/502* (2013.01); *A61K 31/5025* (2013.01); *A61K 31/55* (2013.01); *A61K 33/243* (2019.01); *C12Q 1/6827* (2013.01); *C12Q 2600/112* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | |
|---|---|---|
| 3,590,028 A | 6/1971 | Arcamone et al. |
| 3,892,790 A | 7/1975 | Tobe et al. |
| 3,904,663 A | 9/1975 | Tobe et al. |
| 4,138,480 A | 2/1979 | Gosalvez |
| 4,946,954 A | 8/1990 | Talebian et al. |
| 4,950,738 A | 8/1990 | King et al. |
| 4,996,337 A | 2/1991 | Bitha et al. |
| 5,091,521 A | 2/1992 | Kolar et al. |
| 5,177,075 A | 1/1993 | Suto et al. |
| 5,295,944 A | 3/1994 | Teicher et al. |
| 5,434,256 A | 7/1995 | Khokhar et al. |
| 5,445,934 A | 8/1995 | Fodor et al. |
| 5,510,270 A | 4/1996 | Fodor et al. |
| 5,527,905 A | 6/1996 | Sugimura et al. |
| 5,539,083 A | 7/1996 | Cook et al. |
| 5,556,752 A | 9/1996 | Lockhart et al. |
| 5,578,832 A | 11/1996 | Trulson et al. |
| 5,633,016 A | 5/1997 | Johnson et al. |
| 5,633,243 A | 5/1997 | Sugimura et al. |
| 5,744,305 A | 4/1998 | Fodor et al. |
| RE36,397 E | 11/1999 | Zhang et al. |
| 6,040,138 A | 3/2000 | Lockhart et al. |
| 6,087,340 A | 7/2000 | Gatti et al. |

(Continued)

FOREIGN PATENT DOCUMENTS

| | | |
|---|---|---|
| EP | 0430402 | 6/1991 |
| EP | 1260520 | 11/2002 |

(Continued)

OTHER PUBLICATIONS

Kudoh et al. (Clinical Cancer Research vol. 5 1999 p. 2526) (Year: 1999).*
Bernardini et al. (Biomedicine and Pharmacotherapy vol. 58 2004 p. 17) (Year: 2004).*
Ledermann et al (N engl J Med vol. 366 p. 1382 Apr. 12, 2012) (Year: 2012).*
European Communication Response from Application No. 12801070. 9, dated Apr. 20, 2017.
European Communication Response from Application No. 14779403. 6, dated May 8, 2017.
Hansen et al., "Clinical significance of homologous recombination deficiency score testing in endometrial cancer patients", 2016, ASCO presentation.

(Continued)

*Primary Examiner* — Katherine D Salmon
(74) *Attorney, Agent, or Firm* — W&C IP

(57) ABSTRACT

The invention relates to methods for detecting inactivation of the DNA Homologous Recombination pathway in a patient, and in particular for detecting BRCA1 inactivation.

28 Claims, 7 Drawing Sheets

(56) References Cited

U.S. PATENT DOCUMENTS

Figure 1:
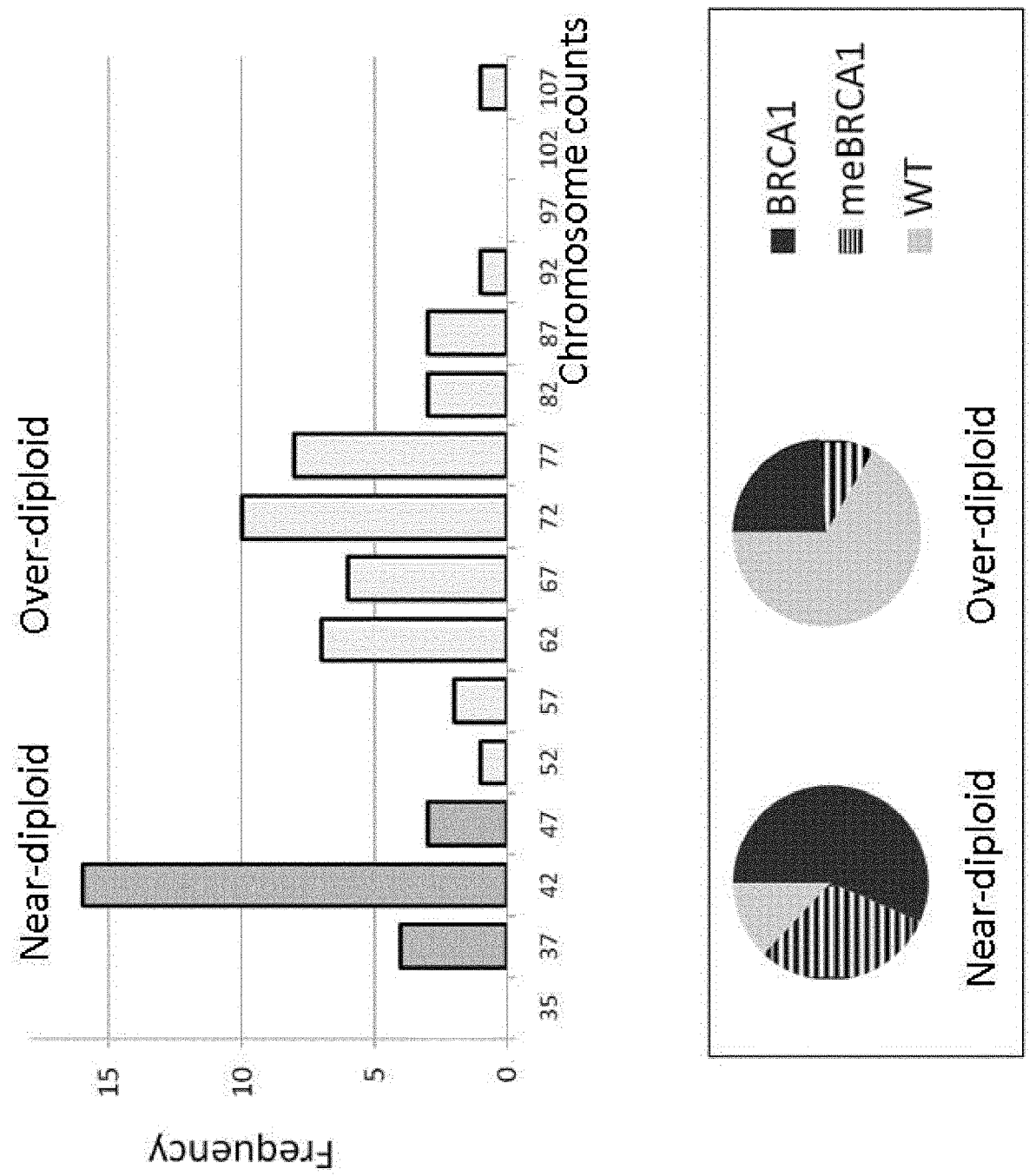

| | | |
|---|---|---|
| 6,210,891 B1 | 4/2001 | Nyren |
| 6,214,821 B1 | 4/2001 | Daoud |
| 6,258,568 B1 | 7/2001 | Nyren et al. |
| 6,274,320 B1 | 8/2001 | Rothberg et al. |
| 6,403,563 B1 | 6/2002 | Geroni et al. |
| 6,455,258 B2 | 9/2002 | Bastian et al. |
| 6,465,177 B1 | 10/2002 | Hoon et al. |
| 6,534,293 B1 | 3/2003 | Barany et al. |
| 7,351,701 B2 | 4/2008 | Helleday et al. |
| 7,485,707 B2 | 2/2009 | Matvienko et al. |
| 7,732,491 B2 | 6/2010 | Sherman et al. |
| 7,754,684 B2 | 7/2010 | Stewart et al. |
| 7,759,488 B2 | 7/2010 | Xiao et al. |
| 7,759,510 B2 | 7/2010 | Kay et al. |
| 7,858,331 B2 | 12/2010 | D'Andrea et al. |
| 7,868,040 B2 | 1/2011 | Wilson et al. |
| 7,915,280 B2 | 3/2011 | Ferraris et al. |
| 9,279,156 B2 | 3/2016 | Gutin et al. |
| 9,574,229 B2 | 2/2017 | Gutin et al. |
| 2003/0049613 A1 | 3/2003 | Perucho et al. |
| 2005/0112604 A1 | 5/2005 | Fujimoto et al. |
| 2006/0088870 A1 | 4/2006 | Finkelstein et al. |
| 2007/0004621 A1 | 1/2007 | Shridhar et al. |
| 2007/0070349 A1 | 3/2007 | Harris et al. |
| 2008/0108057 A1 | 5/2008 | Griffith et al. |
| 2009/0081237 A1 | 3/2009 | D'Andrea et al. |
| 2009/0246789 A1 | 10/2009 | Buckhaults et al. |
| 2010/0145894 A1 | 6/2010 | Semizarov et al. |
| 2010/0159466 A1 | 6/2010 | Eng et al. |
| 2012/0015050 A1 | 1/2012 | Abkevich et al. |
| 2013/0281312 A1 | 10/2013 | Richardson et al. |
| 2015/0080260 A1 | 3/2015 | Abkevich et al. |

FOREIGN PATENT DOCUMENTS

| | | |
|---|---|---|
| EP | 2981624 | 2/2016 |
| JP | 2014-548965 | 10/2016 |
| JP | 2014-548965 | 8/2017 |
| JP | 6117194 | 10/2017 |
| JP | 2014-548965 | 11/2017 |
| KR | 100925337 | 11/2009 |
| WO | 1995020952 | 8/1995 |
| WO | 1998041531 | 9/1998 |
| WO | 1999054498 | 10/1999 |
| WO | 2000024933 | 4/2000 |
| WO | 2003074723 | 9/2003 |
| WO | 2004042032 | 5/2004 |
| WO | 2004/075833 A2 | 9/2004 |
| WO | 2006098978 | 9/2006 |
| WO | 2006110855 | 10/2006 |
| WO | 2006116341 | 11/2006 |
| WO | 2006128195 | 11/2006 |
| WO | 2007035893 | 3/2007 |
| WO | 2009033178 | 3/2009 |
| WO | 2009073869 | 6/2009 |
| WO | 2009148528 | 12/2009 |
| WO | 2010051318 | 5/2010 |
| WO | 2011048495 | 4/2011 |
| WO | 2011106541 | 9/2011 |
| WO | 2011160063 | 12/2011 |
| WO | 2012019000 | 2/2012 |
| WO | 2012027224 | 3/2012 |
| WO | 2012/092426 A1 | 7/2012 |
| WO | 2013/096843 A1 | 6/2013 |
| WO | 2013130347 | 9/2013 |
| WO | 2013182645 | 12/2013 |
| WO | 2014/165785 A2 | 10/2014 |
| WO | 2015/086473 A1 | 6/2015 |
| WO | 2015/108986 A1 | 7/2015 |

OTHER PUBLICATIONS

Lheureux et al., American Association for Cancer Research, 2017, pp. 1-38.

Mills et al., Homologous Recombination Deficiency (HRD) Score Shows Superior Association with Outcome Compared to its Individual Score Components (LOH, TAI, and LST Scores) in Platinum Treated Serous Ovarian Cancer, Annual Meeting on Women's Cancer, 2016, pp. 1-19.

Shahda et al., "Homologous Recombination Deficiency (HRD) in Patients with Pancreatic Cancer and Response to Chemotherapy", 2017, ASCO presentation.

Timms et al., "DNA repair deficiences in ovarian cancer: Genomic analysis of high grade serous ovarian tumors from the NOVA Study", 2015, ESMO presentation.

Timms et al., "The Molecular Landscape of Genome Instability in Prostate Cancer", 2016, ESMO presentation.

Timms et al., Breast Cancer Research, 2014, vol. 16, No. 475, pp. 1-9.

Timms, Declaration Under 37 C.F.R. § 1.132, 2016, pp. 1-3.

Japanese Office Action Response from Application No. 2014-548965, dated Apr. 27, 2017.

Marsit et al; Inactivation of the Fanconi anemia/BRCA pathway in lung and oral cancers: implications for treatment and survival; Oncogene; 2004; 23(4):1000-1004.

Mateo et al., "Appraising iniparib, the PARP inhibitor that never was—what must we learn?," Nature, Dec. 2013, 10: 688-696.

Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004).

McVean et al., Philos Trans R Soc Land B Biol Sci. 365(1544):1213-8 (2010). "What drived recombination hotspots to repeat DNA in humans?".

Meadows et al. "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011 (Apr. 8, 2011), pp. 434-439.

Medri, L. et al. modern Pathology 2003;16(11):1067-1075.

Meindl et al; Germline mutations in breast and ovarian cancer pedigrees establish RAD51C as a human cancer susceptibility gene; Nat Genet; 2010; 42(5):410-414.

Mendes-Pereira et al; Synthetic lethal targeting of PTEN mutant cells with PARP inhibitors; EMBO Mol Med; 2009;1(6-7): 315-322.

Mukhopadhyay et al., "Clinicopathological Features of Homologous Recombination-Deficient Epithelial Ovarian Cancers: Sensitivity to PARP Inhibitors, Platinum, and Survival;" Cancer Research, 2012, 5675-5682.

Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-1908.

Nannya et al. "A Robust Algorithm for Copy Number Detection Using High-Density Oligonucleotide Single Nucleotide Polymorphism Genotyping Arrays", Cancer Research, American Association for Cancer Research, US, vol. 65, No. 14, Jul. 14, 2005 (Jul. 14, 2005), pp. 6071-6079.

Narayan et al; Frequent promoter of methylation of CDH1,DAPK,RARB, and HIC1 genes in carcinoma of cervix uteri: its relationship to clinical outcome; Mol Cancer; 2003;2:24, 12 pages.

Norquist et al; Secondary somatic mutations restoring BRCA1/2 predict chemotherapy resistance in hereditary ovarian carcinomas; J Clin Oncol;2011; 29(22): 3008-3015.

Novak Urban et al: "A high-resolution allelotype of B-cell chronic lymphocytic leukemia (B-CLL)", Blood, American Society of Hematology, US, vol. 100, No. 5, Sep. 1, 2002, pp. 1787-1794.

Ogston et al., Breast. 2(5):320-7 (2003). "A new histological grading system to assess response of breast cancers to primary chemotherapy, prognostic significance and survival."

Osborne et al., "A genome-wide map showing common regions of loss of heterozygosity/allelic imbalance in breast cancer", Cancer Research, vol. 60, No. 14, pp. 3706-3712 (2000).

O'Shaugnessy et al; Iniparib plus chemotherapy in metastatic triple-negative breast cancer; N Engl J Med; 2011; 364(3):205-214.

(56) References Cited

OTHER PUBLICATIONS

Ott et al., Clinical Cancer Research, the American Association for Cancer Research, US, 9(6):2307-2315 (2003). "Chromosomal Instability rather than p53 mutation is associated with response to neoadjuvant cisplatin-based chemotherapy in gastric carcinoma".
Patel et al., "Failure of Iniparib to Inhibit Poly(ADP-Ribose) Polymerase in Vitro," Clin Cancer Res, Mar. 2012, 1655-1662.
Patocs, A. et al., "Breast-cancer stromal cells with TP53 mutations and nodal metastases", N. Engl. J. Med., 2007, vol. 357, pp. 2543-2551.
Peng et al., "Genome-wide transcriptome profiling of homologous recombination DNA repair," Nature Communications, 2014, 1-11.
Pfeifer et al. "Genome-wide analysis of DNA copy number changes and LOH in CLL using high-density SNP arrays", Blood, vol. 109, No. 3, Oct. 5, 2006 (Oct. 5, 2006), pp. 1202-1210.
Popova et al. Cancer Research 72(21); 5454-62; Nov. 1, 2012.
Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."
R. Mei: "Genome-wide detection of Allelic Imbalance Using Human SNPs and High-density DNA arrays", Genome Research, vol. 10, No. 8, Aug. 1, 2000, pp. 1126-1137.
Ramirez, C. et al., "Loss of 1p, 19q, and 10q heterozygosity prospectively predicts prognosis of oligodendroglial tumors—towards individualized tumor treatment?" Neuro. Oncol., May 2010, vol. 12, No. 5, pp. 490-499.
Richard et al., Micro Biol Rev. 72(4):686-727 (2008). "Comparitive genomics and molecular dynamics of DNA repeats in eukaryotes."
Richardson et al., Cancer Cell 9:121-132 (2006). "X chromosomal abnormalities in basal-like human breast cancer."
Ryan et al, 2009 ASCO Annual Meeting, http://meetinglibrary.asco.org/content/34135-65, (2009). "Neoadjuvant cisplatin and bevacizumab in triple negative breast cancer (TNBC): Safety and efficacy."
Sakai et al; Functional restoration of BRCA2 protein by secondary BRCA2 mutations in BRCA2-mutated ovarian carcinoma; Cancer Res; 2009; 69(16):6381-6386.
Sakai et al; Secondary mutations as a mechanism of cisplatin resistance in BRCA2-mutated cancers; Nature; 2008; 451(7182):1116-1120.
Samouelian et al., Cancer Chemother Pharmacol. 54(6): 497-504 (2004). "Chemosensitivity and radiosensitivity profiles of four new human epithelial ovarian cancer cell lines exhibiting genetic alterations in BRCA2, TGFbetaRII, KRAS2, TP53 and/or CDNK2A."
Santana-Davila, R. et al. Journal of Hematology & Oncology 3:42 (Oct. 27, 2010).
Schouten et al., "Challengers in the Use of DNA Repair Deficiency as a Biomarker in Breast Cancer," Journal of Clinical Oncology, 2015, 33(17): 1867-1869.
Schwartz et al., Genes Development 19:2715-2726 (2005). "Homologous recombination and nonhomologous end-ioining repair pathways regulate fragile site stability."
Sebat et al., Science. 305(5683):525-8 (2004). "Large-scale copy number polymorphism in the human genome."
Silva et al., "Loss of heterozygosity in BRCA1 and BRCA2 markers and high-grade malignancy in breast cancer," Breast Cancer Res. & Treatment, Jan. 1999, vol. 53, No. 1, pp. 9-17.
Silver et al. "Efficacy of Neoadjuvant Cisplatin in Triple-Negative Breast Cancer", J. Clin. Oncol. vol. 28, 2010, pp. 1145-1153.
Silver et al., Cell 128(5):991-1005 (2007). "Further evidence for BRCA1 communication with the inactive X chromosome."
Sorlie et al., PNAS 100(14):8418-8423 (2003). "Repeated observation of breast tumor subtypes in independent gene expression data set."
Soule H.D. et al. Cancer Research, 50. 6075-6086. Sep. 15, 1990.
Stankiewicz et al., Am J Hum Genet. 72(5):1101-16 (2003). "Genome architecture catalyzes nonrecurrent chromosomal rearrangements."
Swisher et al. Cancer Res. 68(8):2581-6 (2008). "Secondary BRCA1 mutations in BRCA1-mutated ovarian carcinomas with platinum resistance."
Tai et al., "High-Throughput Loss-of-Heterozygosity Study of Chromosome 3p in Lung Cancer Using Single-Nucleotide Polymorphism Markers", Cancer Research, vol. 66, No. 8, Apr. 15, 2006, pp. 4133-4138.
Takahashi, Clinical Cancer Research, 13(1): 111-120 (2007). "Clonal and Parallel Evolution of Primary Lung Cancers and Their Metastases Revealed by Molecular Dissection of Cancer Cells."
Tan et al; 'BRCAness' syndrome in ovarian cancer: a case-control study describing the clinical features and outcome of patients with epithelial ovarian cancer associated with BRCA1 and BRCA2 mutations; J Clin Oncol; 2008;26(34):5530-5536.
Tassone et al., Br J Cancer. 88(8): 1285-91 (2003). "BRCA1 expression modulates chemosensitivity of BRCA1-defective HCC1937 human breast cancer cells."
Teh M-T et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005 (Oct. 1, 2005), pp. 8597-8603.
Telli et al., "Phase II Study of Gemcitabine, Carboplatin, and Iniparib as Neoadjuvan Therapy for Triple-Negative and BRCA1/2 Mutation-Associated Breast Cancer With Assessment of a Tumor-Based Measure of Genomic Instability: PrECOG0105," J Clin Oncol, 2015, 1-7.
The Cancer Genome Atlas Research Network; Integrated genomic analyses of ovarian carcinoma; Nature; 2011; 474(7353):609-615.
Ashworth, "A Synthetic Lethal Therapeutic Approach: Poly(ADP) Ribose Polymerase Inhibitors for the Treatment of Cancers Deficient in DNA Double-Strand Break Repair," 26(22):3785-3790 (2008) XP055039560.
Bryant et al., "Specific killing of BRCA2-deficient tumours with inhibitors of poly(ADP-ribose) polymerase," Nature, 434(7035):913-917 (2005) XP007906257.
Calvert et al., "245 Invited PARP inhibitors in cancer treatment," Eur. J. Cancer, 6(12):80 (2008) XP025534307.
De Soto et al., "The inhibition and treatment of breast cancer with poly (ADP-ribose) polymerase (PARP-1) inhibitors," Int. J. Biol. Sci., 2(4):179-185 (2006) XP007906272.
Graziani et al., "PARP-1 inhibition to treat cancer, ischemia, inflammation," Pharmacol. Res., 52:1-4 (2005) XP004902631.
Gudmundsdottir et al., "The roles of BRCA1 and BRCA2 and associated proteins in the maintenance of genomic stability," Oncogene, 25:5864-5874 (2006) XP055040467.
International Search Report in PCT/EP2013/061707 dated Jul. 29, 2013.
Joosse et al., "Prediction of BRCA1-association in hereditary non-BRCA1/2 breast carcinomas with array-CGH," Breast Cancer Res. Treat., 116:479-489 (2008) XP019727887.
Penning et al., "Discovery and SAR of 2-(1-propylpiperidin-4-yl)-1H-benzimidazole-4-carboxamide: A potent inhibitor of poly(ADP-ribose) polymerase (PARP) for the treatment of cancer," Bioorganic & Medicinal Chemistry, 16(14):6965-6975 (2008) XP022941564.
Popova et al., "Genome Alteration Print (GAP): a tool to visualize and mine complex cancer genomic profiles obtained by SNP arrays," Genome Biology, 10(11):R128 (2009) XP021065372.
Rakha et al., "Basal-like breast cancer: a critical review," J. Clin. Oncol., 26(15):2568-2581 (2008) XP002661082.
Smid et al., "Patterns and incidence of chromosomal instability and their prognostic relevance in breast cancer subtypes," Breast Cancer Res. Treat., 128(1):23-30 (2010) XP019916000.
Stefansson et al., "Genomic profiling of breast tumours in relation to BRCA abnormalities and phenotypes," Breast Cancer Res., 11(4):R47 (2009) XP021061312.
Vollebergh et al., "Genomic instability in breast and ovarian cancers: translation into clinical predictive biomarkers," Cell. Mol. Life Sci., 69(2):223-245 (2011) XP019993251.
European Communication from Application No. 12801070.9, dated Dec. 22, 2016.
Birkbak et al., "Amount of Allelic Imbalance Predicts Response to Cisplatin in Breast and Ovarian Cancer", Annals of Oncology 21 (2010).
Canadian Office Action from Application No. 2,802,882, dated Feb. 24, 2017.

(56) References Cited

OTHER PUBLICATIONS

European Communication Response, for application 12860530.0, dated Mar. 17, 2017.
Tseng, R. C. et al., Genomewide loss of heterozygosity and its clinical associations in non-small cell lung cancer, Int. J. Cancer, Nov. 1, 2005, vol. 117, No. 2, pp. 241-247.
Tuna, M. et al. PLoS One 5(11):e15094 (Nov. 30, 2010).
Turner et al., Oncogene 26:2126-2132 (2007). "BRCA1 dysfunction in sporadic basal-like breast cancer."
Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005 (Mar. 1, 2005), pp. 87-92.
Van Loo et al., PNAS 107(39):16910-16915 (2010). "Allele-specific copy number analysis of tumors."
Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 12, 2009, pp. 4143-4149.
Vrieling et al., Nature Genetics 28:101-102 (2001). "Mitotic maneuvers in the light."
Walsh, C.S. et al. Clin Cancer Res 14(23):7645 (Dec. 1, 2008).
Wang et al., Cancer Research 64:64-71 (2004). "Loss of heterozygosity and it's correlation with expression in profiles in subclasses of invasive breast cancers."
Wang et al., Genome Biology 8R246 (2007). "Analysis of molecular inversion probe performance for allele copy number determination."
Wilcox et al; High-resolution methylation analysis of the BRCA1 promoter in ovarian tumors; Cancer Genet Cytogenet; 2005; 159(2): 114-122.
Wilcoxen et al., "Homologous recombination deficiency (HRD) score enriches for niraparib sensitive high grade ovarian tumors," Supplemental Abstract, 2015, 1 page.
Wilcoxen et al., "Use of homologous recombination deficiency (HRD) score to enrich for niraparib sensitive high grade ovarian tumors," J Clin Oncol, 2015, Supplemental Abstract: 5532, 2 pages.
Xiao et al., "The XIST Noncoding RNA Functions Independently of BRCA1 in X Inactivation," Cell, Mar. 2007, 128:977-989.
Xu et al., Molecular Cell 3:389-395 (1999). "Centrosome amplification and a defective G2-M cell cycle checkpoint induce genetic instability in BRCA1 Exon 11 Isoform-deficient cells."
Yang et al., Cancer Research 61:348-354 (2001). "Reconstitution of caspase 3 sensitizes MCF-7 Breast Cancer to Doxoubicin- and Etoposide-induced apoptsis."
Yaris N. et al. The Turkish Journal of Pediatrics 2004; 46: 182-185.
Zhao, Q. et al., "Systematic detection of putative tumor suppressor genes through the combined use of exome and transcriptome sequencing", Genome Biol., 2010, vol. 11: R114, pp. 1-14.
Anonymous: "Myriad's HRD Test Significantly Predicts Response to Cisplatin Treatment in Patients with Triple Negative Breast Cancer in Second Research Study", Myriad, Dec. 2013.
European Communication Response, for application 15189527.3, dated Sep. 30, 2016.
European Communication, for application 128060530.0, dated Nov. 28, 2016.
Extended European Search Report, from Application EP14779403.6, dated Oct. 28, 2016.
Extended European Search Report, from Application EP16166825.6 dated Nov. 11, 2016.
Telli et al: "Abstract PD09-04: Homologous Recombination Deficiency (HRD) score predicts pathologic response following neoadjuvant platinum-based therapy in triple-negative and BRCA1/2 mutation-associated breast cancer (BC)", Cancer Research, Dec. 2012.
Abkevich et al. "Patterns of genomic loss of heterozygosity predict homologous recombination repair defects in epithelial ovarian cancer", British Journal of Cancer, vol. 107, No. 10, Oct. 9, 2012, pp. 1776-1782.
Abkevich et al. "Supplemental Material: Table S1: Validation of copy number determinations by Real Time PCR SNP ID Adjacent Gene Sample Copy Number by Real-Time PCR Copy Number by CCNT SNP A", -1712744 CDKN2A HF505 0.010 0.47 HF1382 0.14 0, Oct. 1, 2006 (Oct. 1, 2006), pp. 5-1713144, XP055085899, Retrieved from the Internet: URL: http://cancerres.aacrjournals.org/content/suppl/2006/10/04/66.19.9428.DC2/Supplementary_Tables_1-5.pdf [retrieved on Oct. 29, 2013].
Al-Mulla et al., "Metastatic recurrence of early-stage colorectal cancer is linked to loss of heterozygosity on chromosomes 4 and 14q" Journal of Clinical Pathology, vol. 59, No. 6, pp. 624-630 (2006).
Argos et al. "Genomewide scan for loss of heterozygosity and chromosomal amplification in breast carcinoma using single-nucleotide polymorphism arrays", Cancer Genetics and Cytogenetics, Vo. 182, No. 2, Apr. 15, 2008, pp. 69-74.
Arlt et al., Molecular and Cellular Biology, 24(15):6701-6709 (2004). "BRCA1 is required for common-fragile-site stability via its G2M checkpoint function."
Bamford et al., British Journal of Cancer 91:355-358 (2004). "The Cosmic (Catalogue of Somatic Mutations in Cancer) database and website."
Beder L B et al.: "Genome-wide analyses on loss of heterozygosity in head and neck squamous cell carcinomas", Laboratory Investigation, vol. 83, No. 1, 2003, pp. 99-105.
Bell et al., Nature 474:609-615 (2011). "Integrated genomic analyses of ovarian carcinoma."
Bengtsson et al., Bioinformatics 25(17):2149-2156 (2009). "A single-array preprocessing methods for estimating full-resolution raw copy numbers from all aftymetrix genotyping arrays including genomeWideSNP 5 &6."
Bentsson et al., BMC Bioinformatics 11:245-262 (2010). "TumorBoost: Normalization of allele-specific tumor copy numbers from a single pair of tumor-normal genotyping microarrays."
Beroukhim et al. "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006), p. 2397.
Birbak et al., Cancer Research, 72(8):1, (2012). Abstract 4823: copy number gain and increased expression of BLM and FANCI is associated with sensitivity to genotoxic chemotherapy in triple negative breast and serous ovarian cancer.
Birkbak et al. "Telomeric allelic imbalance indicates defective DNA repair and sensitivity to DNA-damaging agents"; Cancer Discov; 2012; 2(4): 366-375.
Bouwman et al., Nature Structural and Molecular Biology 17(6):688-696 (2010). "53BP1 loss rescues BRCA1 deficiency and is associated with triple-negative and BRCA-mutated breast cancers."
Buch H N et al.: "Prediction of recurrence of nonfunctioning pituitary tumours by loss of heterozygosity analysis", Clinical Endocrinology, vol. 61, 2004, p. 19-22.
Bunting et al., Cell 141(2):243-54 (2010). "53BP1 inhibits homologous recombination in Brca1-deficient cells by blocking resection of DNA breaks."
Burger et al. Drug Resistance Updates 14:22-34 (2011). "Drug transporters of platinum-based anticancer agents and their clinical significance."
Byrski et al., Breast Cancer Res Treat. 115(2):359-63. (2009). "Response to neoadjuvant therapy with cisplatin in BRCA1-positive breast cancer patients."
Carr J. et al. Cancer Genetics and Cytogenetics 172 (2007) 127-138.
Cass et al., Cancer 97(9):2187-95 (2002). "Improved survival in women with BRCA-associated ovarian carcinoma."
Cerbinskaite et al; Defective homologous recombination in human cancers; Cancer Treat Rev; 2012; Epub 2011; 38(2): 89-100.
Cha et al., Science; 297(5581):602-6 (2002). "ATR homolog Mec1 promotes fork progression, thus averting breaks in replication slow zones."
Chang et al., "Assessment of plasma DNA levels, allelic imbalance, and CA 125 as diagnostic tests for cancer", Journal of the National Cancer Institute, vol. 94, No. 22, pp. 1697-1703 (2002).
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005 (Feb. 1, 2005), pp. 510-515.

(56) References Cited

OTHER PUBLICATIONS

Choi et al., "Genetic Classification of Colorectal Cancer Based on Chromosomal Loss and Microsatellite Instability Predicts Survival," Clinical Cancer Research, Jul. 2002, 8: 2311-2322.
Dann et al; BRCA1/2 mutations and expression: response to platinum chemotherapy in patients with advanced stage epithelial ovarian cancer; Gynecol Oncol; 2012;125(3):677-682.
De Preter et al. Cancer Letters 197 (2003) 53-61.
Edwards et al; Resistance to therapy caused by intragenic deletion in BRCA2; Nature; 2008; 451(7182):1111-1115.
Etemadmoghadam et al: "Integrated genome-wide DNA copy number and expression analysis identifies distinct mechanisms of primary chemoresistance in ovarian carcinomas", Clinical Cancer Research, the American Association for Cancer Research, US, vol. 15, No. 4, Feb. 15, 2009 (Feb. 15, 2009), pp. 1417-1427.
European Communication Response for application 11757992.0, dated Mar. 21, 2014.
European Communication Response for application 11757992.0, dated Dec. 9, 2014.
European Communication Response for application 11796544.2, dated Sep. 28, 2015.
European Communication Response, for application 11796544.2, dated Feb. 1, 2016.
European Communication Response, for application 11796544.2, dated Aug. 3, 2015.
European Communication Response, for application 12860530.0, dated Feb. 10, 2016.
European Communication, for application 11757992.0, dated Aug. 5, 2014.
European Communication, for application 11757992.0, dated Dec. 10, 2013.
European Communication, for application 11796544.2, dated Jan. 20, 2016.
European Communication, for application 11796544.2, dated May 11, 2015.
European Communication, for application 11796544.2, dated Sep. 11, 2015.
European Communication, for application 12801070.9, dated Apr. 1, 2016.
European Intention to Grant, for application 11757992.0, dated Jul. 28, 2015.
European Intention to Grant, for application 11796544.2, dated Mar. 31, 2016.
Extended European Search Report, app. No. 12801070.9, dated Dec. 3, 2014.
Extended European Search Report, for application EP11796544.2, dated Nov. 18, 2013.
Extended European Search Report, for application EP15189527.3, dated Mar. 31, 2016.
Extended European Search Report, from Application EP11748075.6 dated Jul. 29, 2013.
Extended European Search Report, from Application EP12860530.0, dated Jul. 24, 2015.
Fang et al. "Genomic Differences Between Estrogen Receptor (ER)-Positive and ER-Negative Human Breast Carcinoma Identified by Single Nucleotide Polymorphism Array Comparative Genome Hybridization Analysis", Cancer, vol. 117, No. 10, May 2011, pp. 2024-2034.
Farmer et al; Targeting DNA repair defect in BRCA mutant cells as a therapeutic strategy; Nature; 2005; 434(7035):917-921.
Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005 (Nov. 1, 2005), pp. 7651-7657.
Ferreira et al: "Array CGH and gene-expression profiling reveals distinct genomic instability patterns associated with DNA repair and cell-cycle checkpoint pathways in Ewing's sarcoma", Oncogene, vol. 27, No. 14, Mar. 27, 2008 (Mar. 27, 2008), pp. 2084-2090.

Filopanti et al., "Loss of heterozygosity at the SS receptor type 5 locus in human GH- and TSH-secreting pituitary adenomas," J. Endocrinol. Invest., Nov. 2004, vol. 27, No. 10, pp. 937-942.
Fontanillas et al., "Key considerations for measuring allelic expression on a genomic scale using high-throughput sequencing", Molecular Ecology, vol. 19, No. 1, Mar. 1, 2010, pp. 212-227.
Franko, J. et al., "Loss of heterozygosity predicts poor survival after resection of pancreatic adenocarcinoma," J. Gastrointest. Surg., Oct. 2008, vol. 12, No. 10, pp. 1664-1723.
Friedenson; BRCA1 and BRCA2 pathways and the risk of cancers other than breast or ovarian; MedGenMed; 2005; 7(2):60, 25 pages.
Gelmon et al; Olaparib in patients with recurrent high-grade serous or poorly differentiated ovarian carcinoma or triple-negative breast cancer: a phase 2, multicentre, open-label, non-randomised study; Lancet Oncol; 2011;12(9):852-861.
Goransson et al. "Quantification of Normal Cell Fraction and Copy Number Neutral LOH in Clinical Lung Cancer Samples Using SNP Array Data", PLOS One, vol. 4, No. 6, Jun. 26, 2009 (Jun. 26, 2009), p. e6057.
Gorringe et al. "Are there any more ovarian tumor suppressor genes? A new perspective using ultra high-resolution copy number and loss of heterozygosity analysis", Genes Chromosomes & Cancer, John Wiley & Sons, NC, US, vol. 48, No. 10, Oct. 1, 2009 (Oct. 1, 2009), pp. 931-942.
Gunnarsson et al. "Large but not small copy-number alterations correlate to high-risk genomic aberrations and survival in chronic lymphocytic lukemia: a high-resolution genomic screening of newly diagnosed patients", Lukemia, vol. 24, No. 1, Jan. 1, 2010 (Jan. 1, 2010), pp. 211-215.
Hampton et al., "Simultaneous assessment of loss of heterozygosity at multiple microsatellite loci using semi-automated fluorescence-based detection: Subregional mapping of chromosome 4 in cervical carcinoma," PNAS, Jun. 1996, vol. 93, No. 13, pp. 6704-6709.
Hastings et al., Nat Rev. Genetic 10(8): 551-564 (2009). "Mechanisms of change in gene copy number."
Castings et al., PLOS Genetics 5(1):e1000327 (2009). "A microhomology-mediated break-induced replication model for the origin of human copy number variation.", pp. 1-9.
Heap et al., "Genome-wide analysis of allelic expression imbalance in human primary cells by high-throughput transcriptome resequencing", Human Molecular Genetics, vol. 19, No. 1, Jan. 1, 2010, pp. 122-134.
Heinsohn, S. et al., "Determination of the prognostic value of loss of heterzygosity at the retinoblastoma gene in osteosarcoma," Int. J. Oncol., May 2007, vol. 30, No. 5, pp. 1205-1214.
Heiser et al., Proc Natl Arad Sci U S A. 109(8):2724-9 (2012). "Subtype and pathway specific responses to anticancer compounds in breast cancer."
Hendricks et al. "'Recombomice': The past, present, and future of recombination-detection in mice" DNA Repair, vol. 3, No. 10, Oct. 5, 2004, pp. 1255-1261.
Hennessy et al; Somatic mutations in BRCA 1 and BRCA2 could expand the No. Of patients that benefit from poly(ADP ribose) polymerase inhibitors in ovarian cancer; J Clin Oncol; 2010; 28(22):3570-3576.
Holstege et al; BRCA1-mutated and basal-like breast cancers have similar aCGH profiles and a high incidence of protein truncating TP53 mutations; BMC Cancer; 2010; 10:654, 15 pages.
Iafrate et al., Nat Genet 36(9): 949-51. (2004). "Detection of large-scale variation in the human genome."
International Preliminary Report on Patentability, app. No. PCT/US2012/071380, dated Apr. 12, 2013.
International Search Report, for application PCT/EP2014/076786, dated Feb. 27, 2015.
International Search Report, for application PCT/US2011/026098, dated Nov. 25, 2011.
International Search Report, for application PCT/US2011/040953, dated Feb. 27, 2012.
International Search Report, for application PCT/US2011/048427, dated Nov. 7, 2011.
International Search Report, for application PCT/US2012/042668, dated Feb. 1, 2013.

(56) References Cited

OTHER PUBLICATIONS

International Search Report, for application PCT/US2012/071380, dated Apr. 12, 2013.
International Search Report, for application PCT/US2013/027295, dated Jun. 10, 2013.
International Search Report, for application PCT/US2015/045561, dated Nov. 9, 2015.
Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.
Janne et al. "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726.
Japanese Patent Application Kohyo Publication No. (JP-A) 2008-538496 (unexamined Japanese national phase publication corresponding to a non-Japanese international publication).
Johansson, P. et al., "Abstract 4833: A genomic portrait of tumor progression using next-generation sequencing", Cancer Res., Apr. 15, 2011, vol. 71, p. 4833.
Juul et al., Cancer Research, 69(24): 509S-510S (2009). "A Genomic Profile Derived Summary Measure of Chromosomal Breakpoints Predicts Response to Treatment with the DNA-Damaging Agent Cisplatin."
Kaklamani et al., "Phase II neoadjuvant clinical trial of carboplatin and eribulin in women with triple negative early-stage breast cancer (NCT01372579)," Breast Cancer Res Treat, 2015, 151:629-638.
Kalb et al., Genome Dyn. 1:218-42. (2006). "Fanconi anemia: causes and consequences of genetic instability."
Kerangueven, F. et al. Cancer Research 57, 5469-5475 (1997).
Ko et al., "Frequent loss of heterozygosity on multiple chromosomes in Chinese esophageal squamous cell carcinomas" Cancer Letters, vol. 170, No. 2, pp. 131-138 (2001).
Kolomietz et al., Genes Chromosomes Cancer. 35(2):97-112 (2002). "The role of Alu repeat clusters as mediators of recurrent chromosomal aberrations in tumors."
Kujawski et al. "Genomic complexity identifies patients with aggressive chronic lymphocytic lukemia", Blood, vol. 112, No. 5, Sep. 1, 2008 (Sep. 1, 2008), pp. 1993-2003.
Lakhani et al., Clin Cancer Res. 11(14)5175-80 (2005). "Prediction of BRCA1 status in patients with breast cancer using estrogen receptor and basal phenotype."
Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.
Leunen et al. "Recurrent Copy number alterations in BRCA1-mutated ovarian tumors alter biological pathways", Human Mutation, vol. 30, n. 12, Dec. 1, 2009 (Dec. 1, 2009), pp. 1693-1702.
Li C. et al. BMC Bioinformatics 2008, 9:204, pp. 1-16.
Li et al., BMC Bioinformatics 12:474 (2011). "Jetset: selecting the optimal microarray probe set to represent a gene."
Li et al., Nature Medicine 15(2):214-219 (2010). "Amplification of LAPTM4B and YWHAZ contributes to chemotherapy resistance and recurrence of breast cancer."
Lin et al. "Integrated analysis of copy number alterations and loss of heterozygosity in human pancreatic cancer using a high-resolution, single nucleotide polymorphism array", Oncology, vol. 75, No. 1-2, Sep. 1, 2008, pp. 102-112.
Loveday et al; Germline mutations in RAD51D confer susceptibility to ovarian cancer; Nat Genet; 2011; 43(9):879-882.
Luo et al., Nat Genet. 26(4):424-9 (2000). "Cancer predisposition caused by elevated mitotic recombination in Bloom mice."
Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000, pp. 842-846.
Maxwell; Peter Maxwell and Associates, Aug. 9, 2017.

Birbak et al: Telomeric Allelic Imbalance Indicates Defective Dna Repair and Sensitivity to DNA-Damaging Agents, American Association for Cancer Research, Cancer Discovery, p. 366-375, Apr. 2012.
Campbell et al: "A genetic variant that disrupts MET transcription is associated with autism", PNAS, vol. 103, No. 45, p. 16834-16839, Nov. 7, 2006.
Karwatsky: Examination Search Report, CIPO, dated Jun. 6, 2017.
Courage: National Phase Application, Response, Berskin & Parr, Aug. 22, 2017.
Duncavage et al: "Hybrid Capture and Next-Generation Sequencing Identify Viral Integration Sites from Formalin-Fixed Paraffin-Embedded Tissue", NGS Viral Insertion Site Discovery, the Journal of Molecular Diagnostics, vol. 13, No. 3 p. 325-333, May 2011.
Helliot: Registered Letter, European Patent Office, Aug. 25, 2017.
Ripaud: Registered Letter, European Patent Office, Aug. 31, 2017.
Botz: Registered Letter, European Patent Office, Sep. 6, 2017.
Aslund: Registered Letter, European Patent Office, Nov. 23, 2017.
Gibson: Claim Amendments, European Patent Office, Sagittarius IP, Jan. 10, 2018.
Cho: PCT Papers, PCT, Jun. 7, 2017.
Johansson et al: "Targeted resequencing of candidate genes using selector probes", Nucleaic Acids Research, vol. 39, No. 2, p. 1-13, 2011.
Juul et al: "Amount of Allelic Imbalance Predicts Response to the Cisplatin in Breast and Ovarian Cancer", Annals of Oncology, vol. 21, supplement 4, May 2010.
Kamat et al: "Chemotherapy induced microsatellite instability and loss of heterozygosity in chromosomes 2, 5, 10, and 17 in solid tumor patients", Cancer Cell International, vol. 14, No. 118, p. 1-9, 2014.
Kiialainen et al: "Performance of Microarray and Liquid Based Capture Methods for Target Enrichment for Massively Parallel Sequencing and SNP Discovery", PLOS One, vol. 6, issue 2, p. 1-10, Feb. 2011.
Ross et al: "Comprehensive next-generation sequencing for clinically actionable mutations from formalin-fixed cancer tissues", Journal of Clinical Oncology, vol. 29, No. 15, p. 1382-1392, Apr. 12, 2012.
Schweiger et al: "Genome-Wide Massively Parallel Sequencing of Formaldehyde Fixed-Paraffin Embedded (FFPE) Tumor Tissues for Copy-Number- and Mutation-Analysis", PLOS One, vol. 4, issue 5, May 2009.
Tommasi et al: "655Val and 1170Pro ERBB2 SNPs in familial breast cancer risk and BRCA1 alterations", Cellular Oncology, vol. 20, p. 241-248, 2007.
Varley et al: "Nested Patch PCR enables highly multiplexed mutation discovery in candidate genes", Cold Spring Harbor Laboratory Press, Genome Research, vol. 18, p. 1844-1850, 2008.
Zuchner et al: "Linkage and association study of late-onset Alzheimer disease families linked to 9p21.3", National Institutes of Health, p. 1-12, Nov. 2008.
Response to Canadian Office Action, Canadian Patent Application No. 2,802,882, dated Feb. 24, 2017.
Erick J. Duncavage et al., "Hybrid Capture and Next-Generation Sequencing Identify Viral Integration Sites from Formalin-Fixed, Paraffin-Embedded Tissue", the Journal of Molecular Diagnostics, vol. 13 No. 3, May 2011, pp. 325-332.
European Communication, EP Application No. 12 801 070.9, dated Aug. 25, 2017.
European Communication, EP Application No. 14 779 403.6, dated Aug. 31, 2017.
European Communication, EP Application No. 12 860 530.0-1403, dated Sep. 6, 2017.
European Communication, EP Application No. 15 757 372.6-1403, dated Nov. 23, 2017.
European Office Communication Response, EP Patent Application No. 15 866 475.5-1403, dated Jan. 10, 2018.
H. Johansson et al., "Targeted resequencing of candidate genes using selector probes," Nucleic Acids Research, 2011, vol. 39, No. 2, pp. 1-13.
Japanese Office Action, Japanese Patent Application No. 2014-548965, dated Oct. 31, 2016.

(56) References Cited

OTHER PUBLICATIONS

Japanese Office Action, Japanese Patent Application No. 2014-548965, dated Aug. 2, 2017.
Japanese Office Action Response, Japanese Patent Application No. 2014-548965, dated Nov. 28, 2017.
N. Juu et al., "Amount of Allelic Imbalance Predicts Response to Cisplatin in Breast and Ovarian Cancer", Annals of Oncology, vol. 21, supplement 4, May 2010.
Nasi Kamat et al., "Chemotherapy induced microsatellite instability and loss of heterozygosity in chrimosomes 2, 5, 10, and 17 in solid tumor patients", Cancer Cell International 2014.
Anna Kiialainen et al., "Performance of Microarray and Liquid Based Capture Methods for Target Enrichment for Massively Parallel Sequencing and SNP Discovery" PLoS One, Feb. 2011, vol. 6, issue 2.
J.S. Ross et al., "Comprehensive next-generation sequencing for clinically actionable mutations from formalin-fixed cancer tissues" Journal of Clinical Oncology, 29, No. 15, May 2011.
Michal R. Schweiger et al., "Genome-Wide Massively Parallel Sequencing of Formaldehyde Fixed-Paraffin Embedded (FFPE) Tumor Tissues for Copy-Number- and Mutation-Analysis" PLoS One, May 2009, vol. 4, Issue 5.
Stefania Tommasi et al., "655Val and 1170Pro ERBB2 SNPs in familial breast cancer risk and BRCA1 alterations" Cellular Oncology 29 (2007) 241-248.
Katherine E. Varley et al., "Nested Patch PCR enables highly multiplexed mutation discovery in candidate genes" Cold Spring Harbor Laboratory Press, 2008, 18:1844-1850.
S. Züchner et al., "Linkage and association study of late-onser Alzheimer disease families linked to 9p21.3" NIH Public Access, Ann Hum Genet. Nov. 2008; 72(Pt. 6): 725.
Written Opposition against Japanese Patent No. 6117194, dated Oct. 19, 2017.
International Search Report—PCT/US2017/023152, dated Jun. 7, 2017.
Canadian Office Action from Application No. 2,860,312 dated Oct. 15, 2018, 6 pages.
European Communication Response from Application No. 17194403. 6, dated Nov. 5, 2018, 5 pages.
M William Audeh, "Novel treatment strategies in triple-negative breast cancer: specific role of poly(adenosine diphosphate-ribose) polymerase inhibition", Pharmacogenomics and Personalized Medicine, 2014:7 pp. 307-316.
Australian Office Action response—Application No: 2012358244, dated Jul. 30, 2018.
European Communication—Application No. 12801070.9-1118, dated Jul. 18, 2018.
European Communication—Application No. 12860530.0-1111, dated May 11, 2018.
European Communication—Application No. 14779403.6-1118, dated Jun. 13, 2018.
European Communication—Application No. 15757372.6-1111, dated Jun. 14, 2018.
European Communication—Application No. 158664755-1111 / 3230472 PCT/US2015064473, dated Jun. 1, 2018.
European Patent Office response—Application No. 12860530.0-1403, dated May 15, 2018.
European Patent Office response—Application No. 12860530.0-1111, dated Jun. 27, 2018.
European Patent Office response—Application No. 15757372.6-1403, dated Jun. 1, 2018.
European Search Report—Application No. 15866475.5-1111 /3230472 PCT/US2015064473, dated May 14, 2018.
Sharoni Jacobs, "Genome-Wide, High-Resolution Detection of Copy Number, Loss of Heterozygosity, and Genotypes from Formalin-Fixed, Paraffin-Embedded Tumor Tissue Using Microarrays", Research Article, 67:6, Mar. 15, 2007, pp. 2544-2551.
European Communication from Application No. 14809384.2, dated Sep. 6, 2018, 5 pages.
European Communication Response from Application No. 14779403. 6, dated Sep. 26, 2018, 12 pages.
Japanese Office Action Response from Application No. 2016-506657, dated Jul. 27, 2018, 10 pages.
Lieberfarb, M.E. et al. Cancer Research 63:4781 (Aug. 2003).
Stronach et al., Molecular Cancer Research, 2018, vol. 16, No. 7, pp. 1103-1111.
Kennedy et al., "The Role of BRCA1 in the Cellular Response to Chemotherapy", Journal of the National Cancer Institute, vol. 96, No. 22, Nov. 17, 2004, pp. 1659-1668.

* cited by examiner

METHODS FOR DETECTING INACTIVATION OF THE HOMOLOGOUS RECOMBINATION PATHWAY (BRCA1/2) IN HUMAN TUMORS

The present application is filed pursuant to 35 U.S.C. 371 as a U.S. National Phase application of International Patent Application No. PCT/EP2013/061707, which was filed Jun. 6, 2013, claiming the benefit of priority to European Patent Application No. 12305648.3, which was filed on Jun. 7, 2012. The entire text of the aforementioned applications is incorporated herein by reference in its entirety.

FIELD OF THE INVENTION

The invention relates to methods for detecting a predisposition to develop cancer and methods for treating cancer.

BACKGROUND OF THE INVENTION

Cancer is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). Cancers can be classified according to the organ, tissue and cell-type from which the cancerous cells originate: lung, colon, liver, skin etc.

Cancer represents one of the leading causes of death in the world. Successful treatment relies on the diagnosis of the disease at very early stages and on the choice of adapted therapies. A plurality of risk factors (lifestyle related, genetic etc.) has been identified for certain types of cancers.

Breast cancer (malignant breast neoplasm) is a type of cancer originating from breast tissue, most commonly from the inner lining of milk ducts or the lobules that supply the ducts with milk. Cancers thought to be originating from ducts are known as ductal carcinomas; those thought to be originating from lobules are known as lobular carcinomas.

Basal-like breast carcinomas (BLCs) are generally described as high grade ductal carcinomas, having so-called triple negative (TNBC) phenotype (absence of estrogen receptor [ER], progesterone receptor [PR] and HER2/ERBB2 overexpression) and characterized by the markers expressed by the normal basal/myoepithelial cells of the mammary gland (such as cytokeratins 5/6, 14, 17 and EGFR (for review,[1,2]).

Breast cancer susceptibility gene BRCA1 has a particular connection to the basal-like phenotype: firstly, BLCs represent the majority of breast carcinomas developing in BRCA1 mutation carriers, while being less than 20% in a sporadic context;[3] secondly, high level of genomic instability observed in BLCs[4-6] goes in line with BRCA1 involvement in double strand break (DSB) signaling and repair by homologous recombination (HR) (for review,[7,8]). However, since HR deficiency (so called BRCAness) has been proposed as a general feature of BLCs[9], such hallmarks as BRCA1 inactivation, high level of genomic instability, and potentially therapeutic response to the treatment exploiting HR deficiency, were found relevant to merely half of BLCs (or TNBCs).[10-15]

Considering its importance in diagnosis and therapeutic stratification, numerous studies attempted to define clinically relevant surrogate markers of BRCAness (for review,[16]). Genomic markers of BRCAness were mainly searched by comparing array-CGH profiles of BRCA1 mutated versus unselected hereditary or sporadic breast tumors.[17-21] Studies comparing BLCs with or without BRCA1 inactivation either found no difference[11,22,23] or identified 3q gain as associated with BRCA1 inactivation[12]. Array-CGH classifier trained on BRCA1 mutated tumors within unselected group of tumors[24] showed approximately 80% sensitivity in the TNBC subgroups in two independent studies.[25,26]

Thus, there is still an unfulfilled need in the art for methods for genomic markers predicting actual BRCA1 inactivation within the group of basal-like breast carcinomas and other cancers.

Recently, Birkbak et al. have described a method for predicting defective DNA repair and response to DNA-damaging agents[60]. This method, called Telomeric allelic imbalance (TAI) is based on the number of allelic imbalances extending to the telomeric end of the chromosome. The main problem of this approach is that it takes into account only chromosomal breaks that lead to telomeric allelic imbalance. Thus, many chromosomal breaks will not contribute to the score, impairing its robustness. Another caveat is that allelic imbalance or loss of heterozygosity of chromosomes prevents detection of telomeric allelic imbalance.

Another recent technology, published as US2012/0015050 (Abkevich), focuses on the loss of heterozygosity as a possible predictive marker of homologuous repair defects in epithelial ovarian cancer. These authors propose to calculate the Homologous Recombination Deficiency score (or "HDR score"), which takes into account the number of regions in which there is a loss of heterozygosity (i.e. only one of the alleles is present). This score does not take into account chromosomal breakpoints or rearrangements which result in allelic imbalance.

SUMMARY OF THE INVENTION

The inventors have discovered that large-scale chromosome breaks are strongly predictive of Homologous Recombination (HR) deficiency, whichever the mechanism of inactivation.

Hence, in one aspect, the invention relates to a method for predicting deficiency in the DNA homologous recombination (HR) pathway in a patient suffering from cancer, comprising the step of quantifying the number of rearrangements in the genomic DNA of a tumor sample obtained from said patient, wherein the number of rearrangements corresponds to the number, per genome, of breakpoints resulting in segments of at least 3 megabases, preferably at least 4 megabases, even more preferably at least 5, 6, 7, 8 9, 10, 11 12, 13, 14, 15, 16, 17, 18, 19 or 20 megabases.

The invention also relates to a method for predicting the efficacy of a treatment in a patient suffering from cancer, wherein said treatment comprises a PARP inhibitor and/or an alkylating agent, and wherein said method comprises the step consisting of predicting deficiency on the HR pathway as described above.

The invention also relates to a PARP inhibitor and/or an alkylating agent for use in a method for treating cancer in a patient wherein said cancer is linked to deficiency in the HR pathway.

The invention also relates to a method for treating cancer in a patient, comprising administering a therapeutically effective amount of a PARP inhibitor and/or an alkylating agent, wherein said patient has been classified as having a deficiency in the HR pathway as described above.

DETAILED DESCRIPTION OF THE INVENTION

Methods for Predicting Deficiency in the DNA Homologous Recombination Pathway

In one aspect, the invention relates to a method for predicting deficiency in the DNA homologous recombination (HR) pathway in a patient suffering from cancer, comprising the step of quantifying the number of rearrangements in the genomic DNA of a tumor sample obtained from said patient, wherein the number of rearrangements corresponds to the number, per genome, of breakpoints resulting in segments of at least 3 megabases, preferably at least 4 megabases, even more preferably at least 5, 6, 7, 8 9, 10, 11 12, 13, 14, 15, 16, 17, 18, 19 or 20 megabases.

Typically, the method of the invention comprises the step of comparing the number of rearrangements per genome to a threshold, wherein a number of rearrangements per genome superior to said threshold is indicative of HR deficiency.

As used herein, the term "patient" denotes a mammal, such as a rodent, a feline, a canine, a bovine, an equine, a sheep, a porcine and a primate. Preferably, a patient according to the invention is a human.

The inventors have observed that tumors from patients suffering from BRCA1 mutations or other deficiencies in the DNA Homologous Recombination pathway are characterized by a genome that contains greater number of breakpoints than control samples or tumors from patients suffering from cancers which do not involve the HR pathway.

More specifically, the inventors have demonstrated that the relevant breakpoints are those which result in genomic DNA segments of at least 10 megabases. According to the invention, the breakpoints which result in smaller segments are not taken into account.

Without wishing to be bound by theory, the inventors believe that, by eliminating the breakpoints resulting in segments of less than 3 megabases, preferably of less than 4 megabases, even more preferably of less than 5, 6, 7, 8, 9, 10, 11 12, 13, 14, 15, 16, 17, 18, 19 or 20 megabases the resulting number of breakpoints (or large-scale transitions) is a more accurate measurement of the genomic instability related to homologous recombination deficiency. Other breakpoints with local concentration are not correlated with the homologous recombination status.

As used herein, the expression "DNA homologous recombination (HR) pathway" has its general meaning in the art. It refers to the pathway through which Double Stranded DNA breaks (DSB) are repaired by a mechanism called Homologous Recombination.

Inside mammalian cells, DNA is continuously exposed to damage arising from exogenous sources such as ionizing radiation or endogenous sources such as byproducts of cell replication. All organisms have evolved different strategies to cope with these lesions. One of the most deleterious forms of DNA damage is DSB. In mammalian cells, there are two major pathways to repair DSB: Homologous recombination (HR) and Non Homologous End Joining (NHEJ). HR is the most accurate mechanism to repair DSB because it uses an intact copy of the DNA from the sister chromatid or the homologous chromosome as a matrix to repair the break.

BRCA1, BRCA2, PALB2/FANCN, BRIP1/FANCJ, BARD1, RAD51 and RAD51 paralogs (RAD51B, RAD51C, RAD51D, XRCC2, XRCC3) are proteins that are important for the repair of double-strand DNA breaks by this error-free HR pathway. When the gene for either protein is mutated, or when one of the genes is under-expressed, the change can lead to errors in DNA repair that can eventually cause cancer. Although not yet found recurrently mutated in human tumors, other actors of the HR pathway may potentially be deregulated in cancers, such as FANCA, FANCB, FANCC, FANCD2, FANCE, FANCG, FANCI, FANCL, FANCM, FAN1, SLX4/FANCP or ERCC1.

Thus, the expression "deficiency in the HR pathway", as used herein, refers to a condition in which one or several of the proteins involved in the HR pathway for repairing DNA is deficient or inactivated.

It encompasses, but is not limited to, inactivation of at least one of the following genes: BRCA1, BRCA2, PALP2/FANCN, BRIP1/FANCJ, BARD1, RAD51, RAD51 paralogs (RAD51B, RAD51C, RAD51D, XRCC2, XRCC3), FANCA, FANCB, FANCC, FANCD2, FANCE, FANCG, FANCI, FANCL, FANCM, FAN1, SLX4/FANCP and ERCC1.

A used herein the expressions "deficiency in the HR pathway" or "tumor deficiency in the HR pathway" are used interchangeably. Indeed, it refers to the genetic status of the tumor cells. However, in the case of germline mutations, said mutations can be found throughout the entire genome of the patient.

As used herein the term "inactivation", when referring to a gene, can mean any type of deficiency of said gene. It encompasses germline mutations in the coding sequence, somatic mutations in the coding sequence, mutations in the promoter and methylation of the promoter.

In one embodiment of the invention, the deficiency in the HR pathway is a BRCA1 mutation. Several BRCA1 mutations have already been described in the art and are known to be associated with certain types of cancer, such as breast and ovary cancers[55].

On another embodiment of the invention, the deficiency in the HR pathway is a BRCA2 mutation[56].

In yet another embodiment of the invention, the deficiency in the HR pathway is hypermethylation of the BRCA1 promoter[57].

As used herein, the term "cancer" has its general meaning in the art. It refers to the pathological condition in mammals that is characterized by unregulated cell growth.

Examples of cancer include, but are not limited to solid tumors or a carcinoma. Preferably, the solid tumor is selected from breast cancer, colon cancer, lung cancer, prostate cancer, renal cancer, metastatic or invasive malignant melanoma, brain tumor, bladder cancer, head and neck cancer and liver cancer. Carcinoma includes bladder, breast, colon, kidney, liver, lung, ovary, pancreas, stomach, cervix, thyroid or skin carcinoma, including squamous cell carcinoma. However, the present invention also contemplates hematopoietic tumors such as leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkitt's lymphoma, acute and chronic myelogenous leukemias and promyelocytic leukemia.

In one embodiment, said cancer is selected from the group consisting of breast cancer, ovary cancer, pancreas cancer, head and neck cancer and melanoma.

In a preferred embodiment, said cancer is selected from the group consisting of breast cancer, ovary cancer, cervix cancer, pancreas cancer and lung cancer.

In a more preferred embodiment, said cancer is a breast cancer.

The tumor sample suitable for carrying out the method of the invention is typically a biopsy obtained from the diseased tissue or organ of the patient suffering from cancer.

Quantification of the Number of Rearrangements

The step of quantifying the number of rearrangements per genome in the genomic DNA of the tumor sample can be performed by any suitable method in the art.

As mentioned above, the inventors have demonstrated that the relevant breakpoints are those which result in genomic DNA segments of at least 3 megabases. Indeed, preferred cut-off points comprised between 9 and 11, even more preferably about 10 megabases, have been described in the Examples below, but similar results were obtained with cutoff value between 3 megabases and 20 megabases. According to the invention, the breakpoints which result in segments of less than these cutoff points are not taken into account.

The skilled person can readily select any method for quantifying genomic rearrangements and filter out the breakpoints that result in genomic DNA segments of less than 3, preferably less than 4, 5, 6, 7, 8, 9, 10, 11, 12, 13, 14, 15, 16, 17, 18, 19, or 20 megabases.

In one embodiment, the step of quantifying rearrangements is carried out by sequencing techniques, such as next-generation sequencing using mate paired libraries, or longer reads.[58]

In another embodiment, the step of quantifying rearrangements is performed by quantifying the number of copy number variations per genome. Typically, this can be done by hybridization techniques such as comparative genomic hybridization (CGH) array and Single Nucleotide Polymorphism (SNP) array.

Suitable methods for quantifying rearrangements include, but are not limited to, those described in Le Scouarnec and Gribble, Heredity, 2012, 108, 75-85.

Evaluation of the Ploidy

In one embodiment, the method of the invention further comprises a step wherein the ploidy of the tumor sample is evaluated.

As used herein, the term "ploidy" has its general meaning in the art. It refers to the mean number of copies of each locus in the genome.

Typically, a healthy cell (and therefore a healthy tissue sample) is diploid, i.e. it contains two copies/two alleles of each locus.

Without wishing to be bound by theory, it is believed that certain types of cancer are characterized by whole genome duplication during cancer progression, resulting in over-diploid (tetraploid or more) tumor cells (Ref 40).

Tumor samples can be split into diploid tumors or near-diploid tumors on the one hand and over-diploid tumors in the other hand.

The inventors have observed that near-diploid tumor genomes were associated in more than 75% of the cases with BRCA1 inactivation (by mutation or by promoter methylation).

Without wishing to be bound by theory, it is believed that diploid or near-diploid tumors are highly predictive of HR-deficient tumors, at least in high grade breast carcinoma.

Typically, a tumor is deemed to be "diploid or near-diploid" if the genome of said tumor carries on average less than 50 chromosomes and/or if had a DNA index close to 1.

Typically, a tumor is considered as "over-diploid" if its genome carries more than or equal to 50 chromosomes and/or has a DNA index higher than 1.2.

As used herein, the term "DNA index" represents the ratio of DNA content of the tumor cell and DNA content of a normal cell.

The skilled person can evaluate the ploidy of a tumor sample according to any standard technique in the art.

Suitable techniques for evaluating ploidy include, but are not limited to:

Measuring the amount of DNA per cell, by example by Fluorescence Activated Cell Sorting.

In this technique, DNA is labeled by incorporation of an intercalating agent such as ethidium bromide or DAPI. The cells are then sorted according to the fluorescence intensity, which is proportional to the amount of DNA in each cell.

karyotyping,

Conventional karyotypes can be obtained by staining the chromosomes (with stains such as Giemsa) and counting the number of chromosomes of each type in a cell.

Virtual karyotyping using arrays such as array-CGH or Single Nucleotide Polymorphism array (SNP array).

The arrays themselves can be genome-wide (probes distributed over the entire genome) or targeted (probes for genomic regions known to be involved in a specific disease) or a combination of both. Further, arrays used for karyotyping may use non-polymorphic probes, polymorphic probes (i.e., SNP-containing), or a combination of both. Non-polymorphic probes can provide only copy number information, while SNP arrays can provide both copy number and loss-of-heterozygosity (LOH) status in one assay. Commercially available oligonucleotide SNP arrays can be solid phase (Affymetrix, Santa Clara, Calif., USA) or bead-based (Illumina, SanDiego, Calif., USA). Despite the diversity of platforms, ultimately they all use genomic DNA from disrupted cells to recreate a high resolution karyotype in silico. The end product does not yet have a consistent name, and has been called virtual karyotyping, digital karyotyping, molecular allelokaryotyping, and molecular karyotyping. Other terms used to describe the arrays used for karyotyping include SOMA (SNP oligonucleotide microarrays) and CMA (chromosome microarray).

Next Generation Sequencing.

High throughput methods for sequence the genome or the complete coding region are available. Whole genome or exome deep sequencing approaches can generate copy number and allelic imbalance profiles similar to or even more precise than SNP arrays.

According to one embodiment of the invention, the step of evaluating the ploidy of the tumor sample is carried out by a technique selected from the group consisting of FACS, karyotyping, and SNP array.

In one embodiment, both the step of evaluating the ploidy and the step of quantifying the number of large-scale rearrangement are performed by SNP array.

In a preferred embodiment, both the step of evaluating the ploidy and the step of quantifying the number of large-scale rearrangement are performed by SNP array, followed by GAP analysis.

Genome Alteration Print (GAP) is a bioinformatics tool which has been developed by Popova et al. (Genome Biology, 2009, 10:R128) for automatic detection of absolute segmental copy numbers and genotype status in complex cancer genome profiles measured with SNP-array. This method performs well even for poor-quality data, low tumor content and highly rearranged tumor genomes.

Two-Step Method

In one embodiment of the invention, the method comprises the step of comparing the number of rearrangements per genome to a threshold, wherein a number of rearrangements resulting in segments of at least 3 megabases (preferably at least 4, 5, 6, 7, 8, 9, 10, 11, 12, 13, 14, 15, 16, 17, 18, 19 or 20) superior to said threshold is indicative of HR deficiency.

Typically, the threshold can have different values, depending on the ploidy of the tumor.

Thus, in a preferred embodiment, the method comprises the step comparing the number of rearrangements in the genomic DNA to a threshold,
wherein said threshold has a first value (threshold1) if the tumor is diploid or near-diploid
and wherein said threshold has a second value (threshold2) if the tumor is overploid.

Typically, threshold1 (as determined using segments longer than 10 megabases, threshold value being dependent of the chosen segment size) can be 15 Large-Scale Transitions (LST) per genome, preferably 16, even more preferably 17, 18, 19 or 20 LST per genome.

Typically, the value of threshold1 may vary, depending on how the number of rearrangements or LSTs is defined. Hence, in one embodiment of the invention, threshold 1 for diploid or near-diploid tumors is defined as follows:
- if the number of LSTs is defined as the number of rearrangements resulting in segments of at least 6 megabases, threshold1 may be 17, 18 or 19;
- if the number of LSTs is defined as the number of rearrangements resulting in segments of at least 7 megabases, threshold1 may be 15, 16 or 17;
- if the number of LSTs is defined as the number of rearrangements resulting in segments of at least 8 megabases, threshold1 may be 14
- if the number of LSTs is defined as the number of rearrangements resulting in segments of at least 9 megabases, threshold1 may be 11, 12, 13 or 14;
- if the number of LSTs is defined as the number of rearrangements resulting in segments of at least 10 megabases, threshold1 may be 11.

Typically, threshold2 (as determined using segments longer than 10 megabases, threshold value being dependent of the chosen segment size) can be 20 Large-Scale Transitions (LST) per genome, preferably 21, even more preferably 22, 23, 24 or 25 LST per genome.

Typically, the value of threshold2 may vary, depending on how the number of rearrangements or LSTs is defined. Hence, in one embodiment of the invention, threshold 2 for overploid tumors is defined as follows:
- if the number of LSTs is defined as the number of rearrangements resulting in segments of at least 6 megabases, threshold1 may be 32;
- if the number of LSTs is defined as the number of rearrangements resulting in segments of at least 7 megabases, threshold1 may be 27, 28 or 29;
- if the number of LSTs is defined as the number of rearrangements resulting in segments of at least 8 megabases, threshold1 may be 26;
- if the number of LSTs is defined as the number of rearrangements resulting in segments of at least 9 megabases, threshold1 may be 19, 20, 21, 22, 23, 24 or 25;
- if the number of LSTs is defined as the number of rearrangements resulting in segments of at least 10 megabases, threshold1 may be 18, 19, 20, 21, 22.

It falls within the ability of the skilled person in the art to determine the optimum thresholds, depending on the size of the LSTs, in order to arrive at optimal specificity and sensitivity according to the tumor type. For example, optimum thresholds for breast carcinoma are 7/17/29, 8/14/26, 9/14/29 or 10/11/22, whereas optimum threshold in ovarian carcinoma is 6/19/32 or 7/17/29 (LST number/threshold1/threshold2).

Indeed, the inventors have found that a 2-step decision rule, wherein the patients are classified according to the ploidy of the tumor, and according to the number of large-scale transitions in the tumor genome, was able to correctly predict HR deficient tumors.

The invention therefore relates to a method comprising the steps of:
- determining the ploidy of the tumor;
- comparing the number of rearrangements per genome to a threshold, wherein a number of rearrangements resulting in segments of at least 3 megabases superior to said threshold is indicative of HR deficiency.

Advantageously, the method according to the invention is able to predict deficiency in the HR pathway with good specificity (few false positives) and good sensitivity (few false negatives).

Methods for Predicting the Efficacy of a Treatment and Methods of Treatment

The method described above has several major and direct clinical applications.

Firstly, tumor genomic profiling can now be used as criteria for genetic testing and council. This is especially important in absence of familial context of tumor predisposition, a situation found in as much as half of mutation-carrier patients[53].

Secondly with the emerging therapeutic perspective exploiting HR defects by targeting complementary pathways (for instance, PARP inhibitors (PARPi)[13], and alkylating agents, which provoke DNA damage), the question of efficient predictive markers of BRCAness or HR deficiency becomes important[16]. The disappointing efficiency of PARPi in unselected BLC/TNBC[54] supports the necessity to better stratify patients, which could be easily implemented using this SNP-array based marker.

Since it is possible to predict whether a given patient suffers from a cancer which is associated with deficiency in the DNA homologous recombination pathway, it is also possible to select the appropriate therapy for said patient.

Indeed, it is believed that a treatment which causes double strand breaks in the DNA (such as alkylating agents) or a treatment which inhibits the alternative DNA repair pathway (such as PARPi) will be more efficient if the tumor is deficient for the HR pathway.

In addition, the inventors have shown that the number of LSTs is a good predictor or response to treatment with an alkylating agent such as cisplatin (see Example 3).

Therefore, another aspect of the present invention concerns a method for predicting the efficacy of a treatment in a patient suffering from cancer, wherein said treatment comprises a PARPi and/or an alkylating agent, and wherein said method comprises the step consisting of predicting deficiency on the HR pathway as described above.

The invention also relates to a PARPi and/or an alkylating agent for use in a method for treating cancer in patient wherein said cancer is linked to deficiency in the HR pathway.

As used herein the term "PARP inhibitor" has its general meaning in the art. It refers to a compound which is capable of inhibiting the activity of the enzyme polyADP ribose polymerase (PARP), a protein that is important for repairing single-strand breaks ('nicks' in the DNA). If such nicks persist unrepaired until DNA is replicated (which must precede cell division), then the replication itself will cause double strand breaks to form. Drugs that inhibit PARP cause multiple double strand breaks to form in this way, and in tumors with BRCA1, BRCA2 or PALB2 mutations these double strand breaks cannot be efficiently repaired, leading to the death of the cells.

Typically, the PARP inhibitor according to the invention can be selected from the group consisting of iniparib, olaparib, rucaparib, CEP 9722, MK 4827, BMN-673, and 3-aminobenzamide.

As used herein, the term "alkylating agent" or "alkylating antineoplastic agent" has its general meaning in the art. It refers to compounds which attach an alkyl group to DNA.

Typically, the alkylating agent according to the invention can be selected from platinum complexes such as cisplatin, carboplatin and oxaliplatin, chlormethine, chlorambucil, melphalan, cyclophosphamide, ifosfamide, estramustine, carmustine, lomustine, fotemustine, streptozocin, busulfan, pipobroman, procarbazine, dacarabazine, thiotepa and temozolomide.

The invention also relates to a method for treating cancer in a patient, comprising administering a therapeutically effective amount of a PARP inhibitor and/or an alkylating agent, wherein said patient has been classified as having a deficiency in the HR pathway as described above.

In one aspect, the invention relates to a method for treating cancer in a patient, comprising the steps of:
- quantifying the number of rearrangements in the genomic DNA of a tumor sample obtained from said patient, wherein the number of rearrangements corresponds to the number, per genome, of breakpoints resulting in segments of at least 3 megabases, preferably at least 4 megabases, even more preferably at least 5, 6, 7, 8 9, 10, 11 12, 13, 14, 15, 16, 17, 18, 19 or 20 megabases.
- comparing said number of rearrangements to a predetermined threshold;
- administering a therapeutically effective amount of a PARP inhibitor and/or an alkylating agent, if said patient has a number of rearrangements superior to said threshold.

As explained above, said threshold may differ, depending on whether the tumor is a diploid or near-diploid tumor, or rather an overploid tumor.

Said threshold may also differ, depending on the minimum size of the segments taken into account for determining the number of rearrangements (or "LSTs").

By a "therapeutically effective amount" of an agent which increases the level of deoxyuridine is meant a sufficient amount to treat cancer, at a reasonable benefit/risk ratio applicable to any medical treatment. It will be understood, however, that the total daily usage of an agent which increases the level of deoxyuridine will be decided by the attending physician within the scope of sound medical judgment. The specific therapeutically effective dose for any particular subject in need thereof will depend upon a variety of factors including other cancer predisposition markers, lifestyle-related risk factors and the activity of the specific agent which increases the level of deoxyuridine to be used, the age, body weight, general health, sex and diet of the subject, the time of administration, route of administration, the duration of the treatment; drugs used in combination or coincidental with the and like factors well known in the medical arts.

The invention also relates to a pharmaceutical composition comprising a PARP inhibitor and/or an alkylating agent for use in a method of treating cancer in a patient, wherein said cancer is linked to deficiency in the HR pathway.

In the pharmaceutical compositions of the present invention for oral, sublingual, subcutaneous, intramuscular, intravenous, transdermal, local or mucosal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and oral administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In one embodiment, the PARP inhibitor and/or alkylating agent is administered in combination with another active agent.

Typically, the PARP inhibitor and the other active agent can be formulated separately. Alternatively, they can be formulated together in a pharmaceutical composition.

In one embodiment, the PARP inhibitor and/or alkylating agent is administered to a patient who is subjected to radiation therapy and/or surgery in order to remove the tumor.

The invention will be further described by the following examples and figures, which are not intended to limit the scope of the protection defined by the claims.

FIGURE LEGENDS

FIG. 1. Chromosome content and BRCA1 status in BLCs. A. Distribution of the chromosome content in the set of BLCs displayed two modes, which evidences 2 populations of tumors with different ploidy status. B. Near-diploid tumors (<50 chromosomes) and over-diploid tumors (>=50 chromosomes) showed different proportions of proven BRCA1-inactivated tumors.
WT correspond to non BRCA1.

Figure 2:
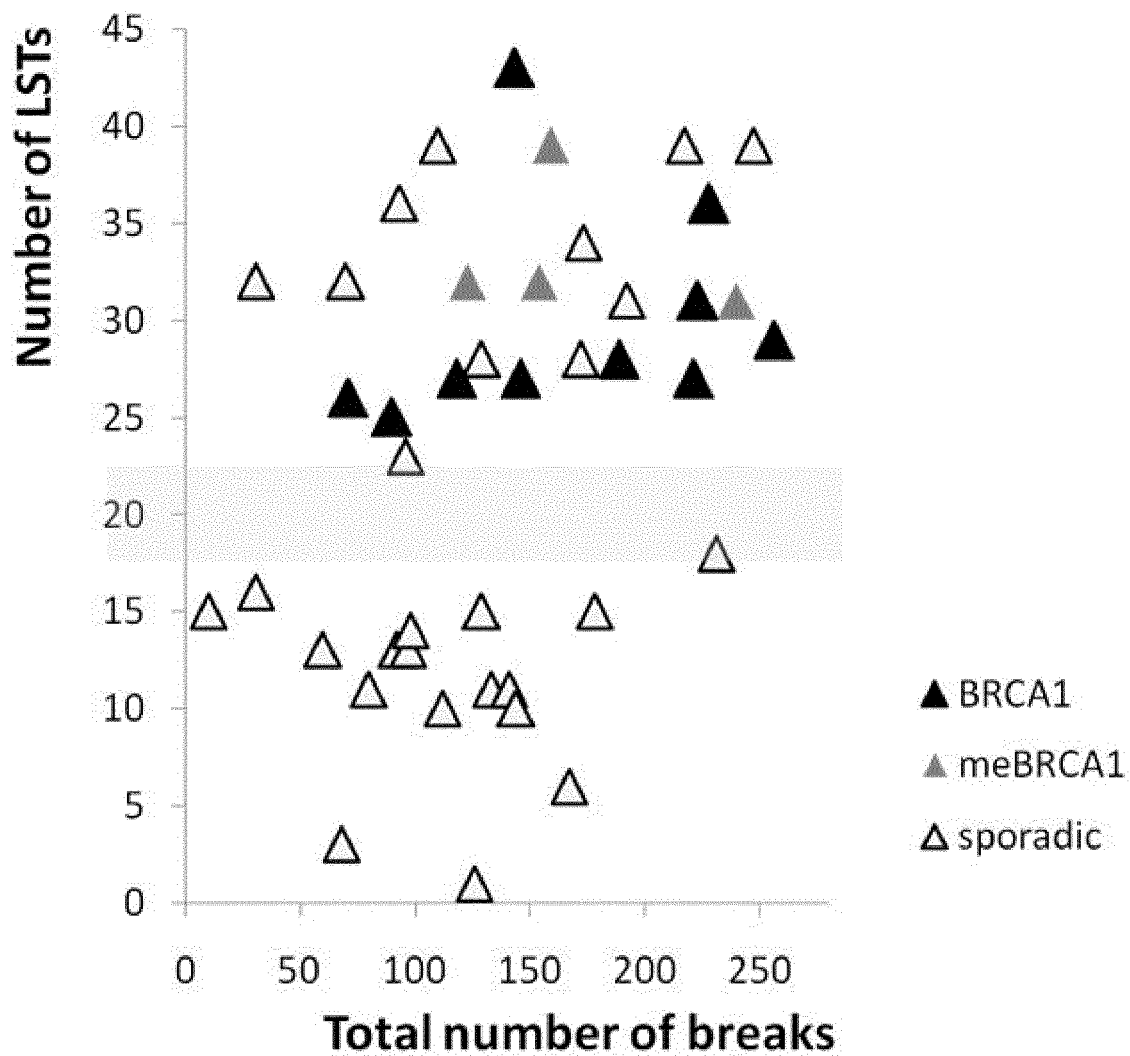

FIG. 2. Genomic instability in over-diploid BLCs as estimated by the total number of breaks and by LSTs. LST number clearly discriminated non-BRCA1 BLCs from BLCs with proven BRCA1 inactivation (p-value<0.001, Wilcoxon test). Total number of breaks was less significantly different between non-BRCA1 vs BRCA1 and meBRCA1 comparison (p-value<0.03, Wilcoxon test) and was not discriminative. BRCA1: germline BRCA1 mutation; meBRCA1: BRCA1 promoter methylation; sporadic=non-BRCA1: absence of evidence of BRCA1 inactivation.

Figure 3:
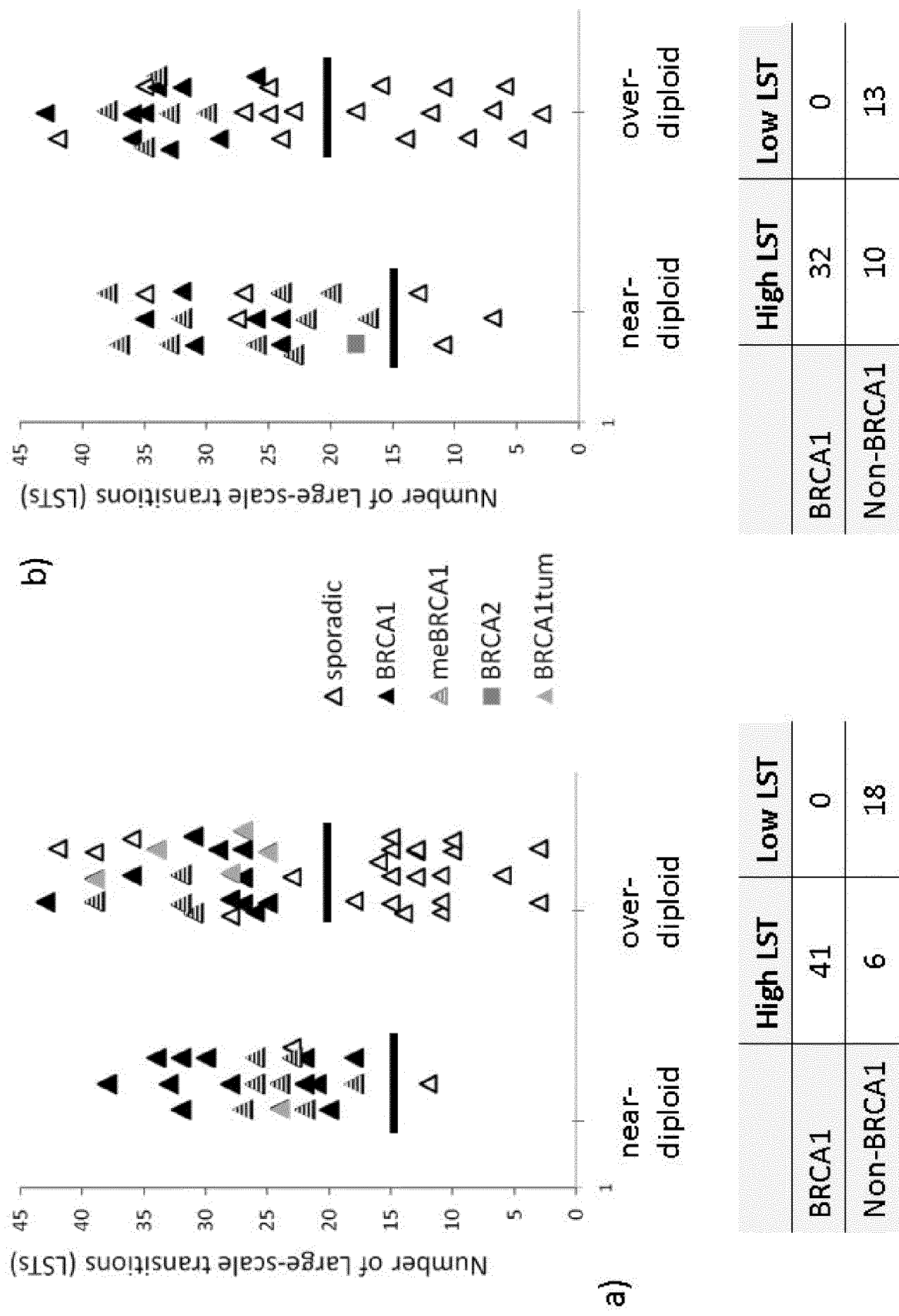

FIG. 3. Tumor ploidy and the number of large-scale transitions (LST) are discriminative of BRCA1 inactivation in the experimental (left) and validation (right) sets. Upper panel: number of LSTs per tumor is indicated in relation to ploidy categories. Near-diploid and near-tetraploid cutoffs are indicated by a bar. Known BRCA1 and BRCA2 statuses are indicated for germline mutations ("BRCA1" and "BRCA2"), methylation of the BRCA1 promoter ("me-BRCA1") and mutations in the tumors ("tumBRCA1"). Tumors without evidence of BRCA1/2 inactivation are referred to as "non-BRCA1". Fisher's exact tests are indicated below the contingency tables; BRCA1 refers to all proven BRCA1-inactivated BLCs, non-BRCA1 refers to BLCs without evidence of BRCA1 inactivation.

Figure 4:
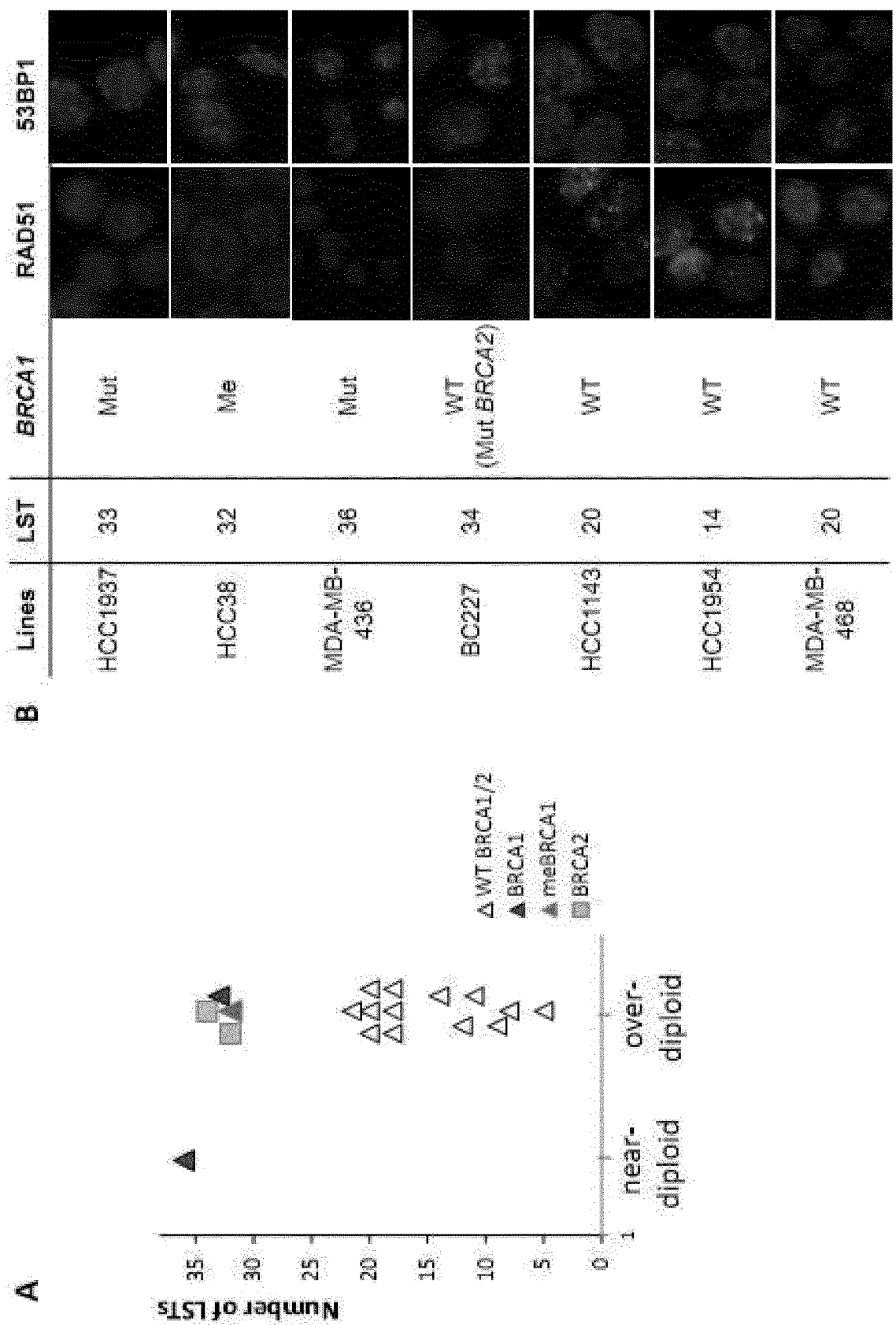

FIG. 4. Genomic and functional assessments of BRCAness in basal-like cell lines. A. Cell lines with basal-like phenotype display discriminative features of BRCAness similar to primary BLCs. Known status for BRCA1 and BRCA2 are indicated for germline mutations ("BRCA1" and "BRCA2") and methylation of BRCA1 promoter ("me-BRCA1"). Cell lines without evidence of BRCA1/2 inactivation are described as "non-BRCA½". B. RAD51 foci formation 8 hours after 10 Gy irradiation illustrates active homologous recombination (HR) in non-BRCA1 cell lines, and conversely deficient HR in BRCA1 or BRCA2 mutated cell lines. 53BP1 foci in the same experiment are shown as a control for DNA damage response. Scale bars, 20 μm). Number of LST is indicated as well as BRCA1/2 status: mut, mutated; me, methylation of the promoter; wt, wildtype.

Figure 5:
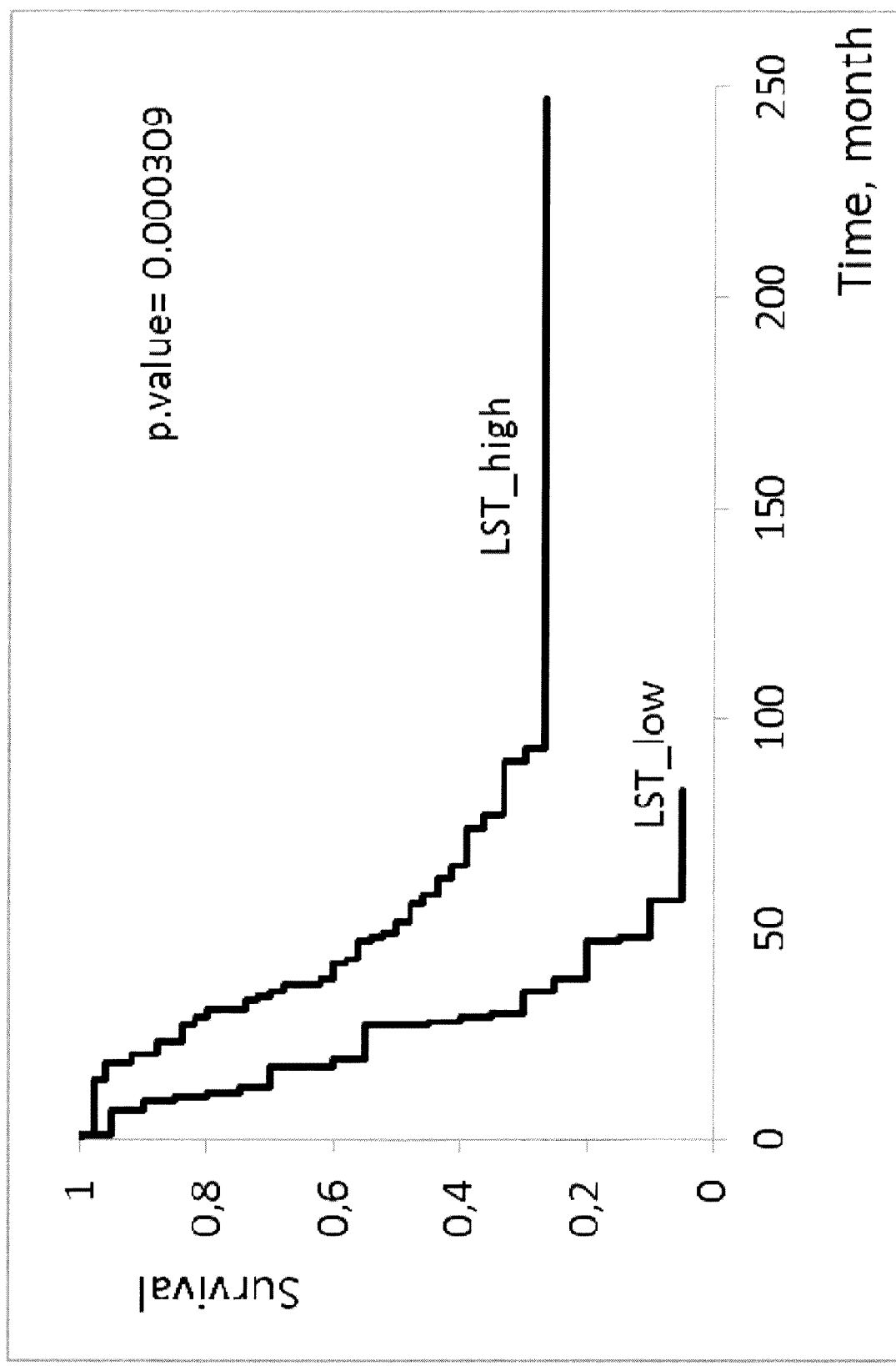

FIG. 5. Survival curves for LST_high and LST_low ovarian tumors. P-value was estimated by log-rank test statistic.

Figure 6:
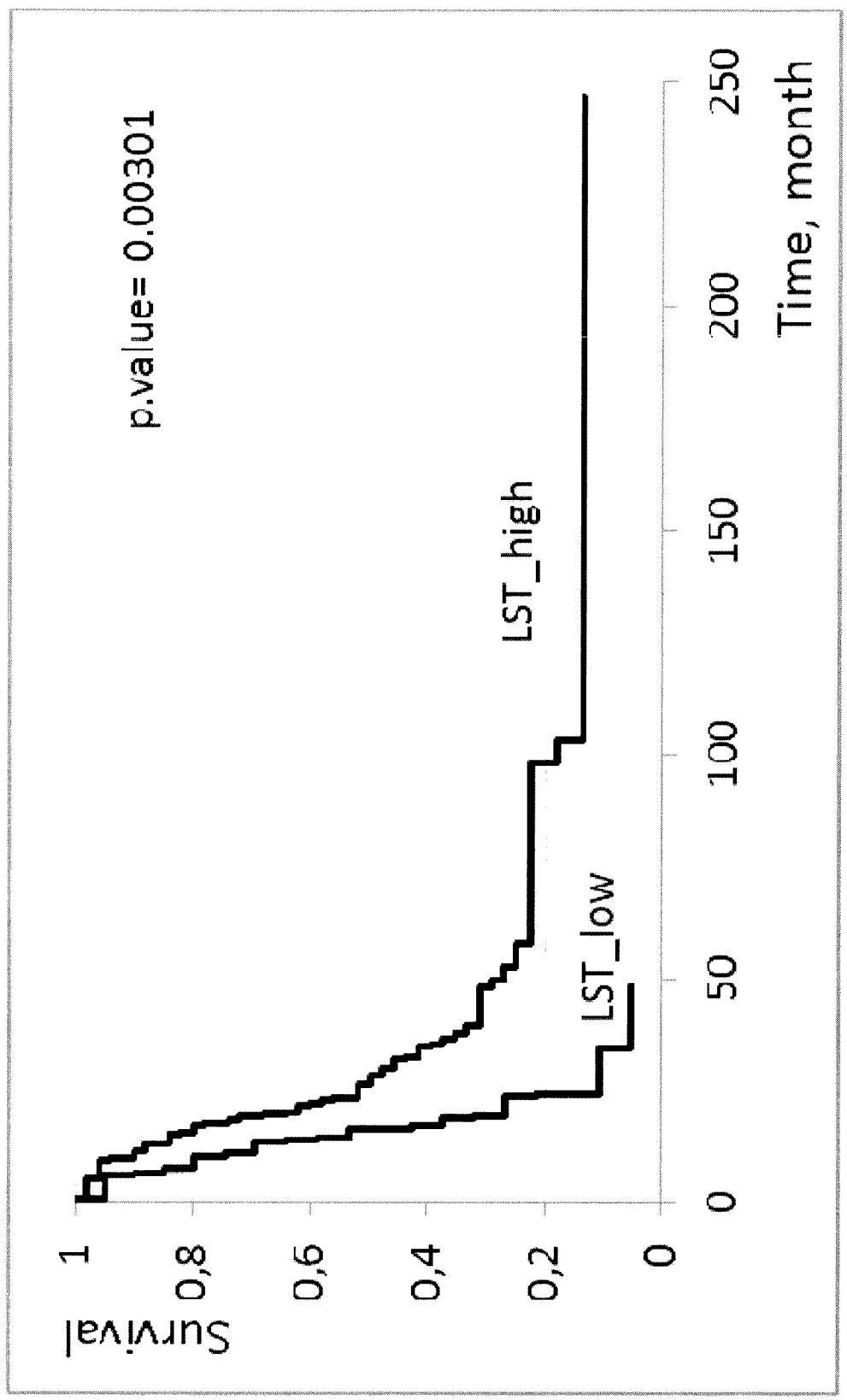

FIG. 6. Event free survival curves for LST_high and LST_low ovarian tumors. P-value was estimated by log-rank test statistic.

Figure 7:
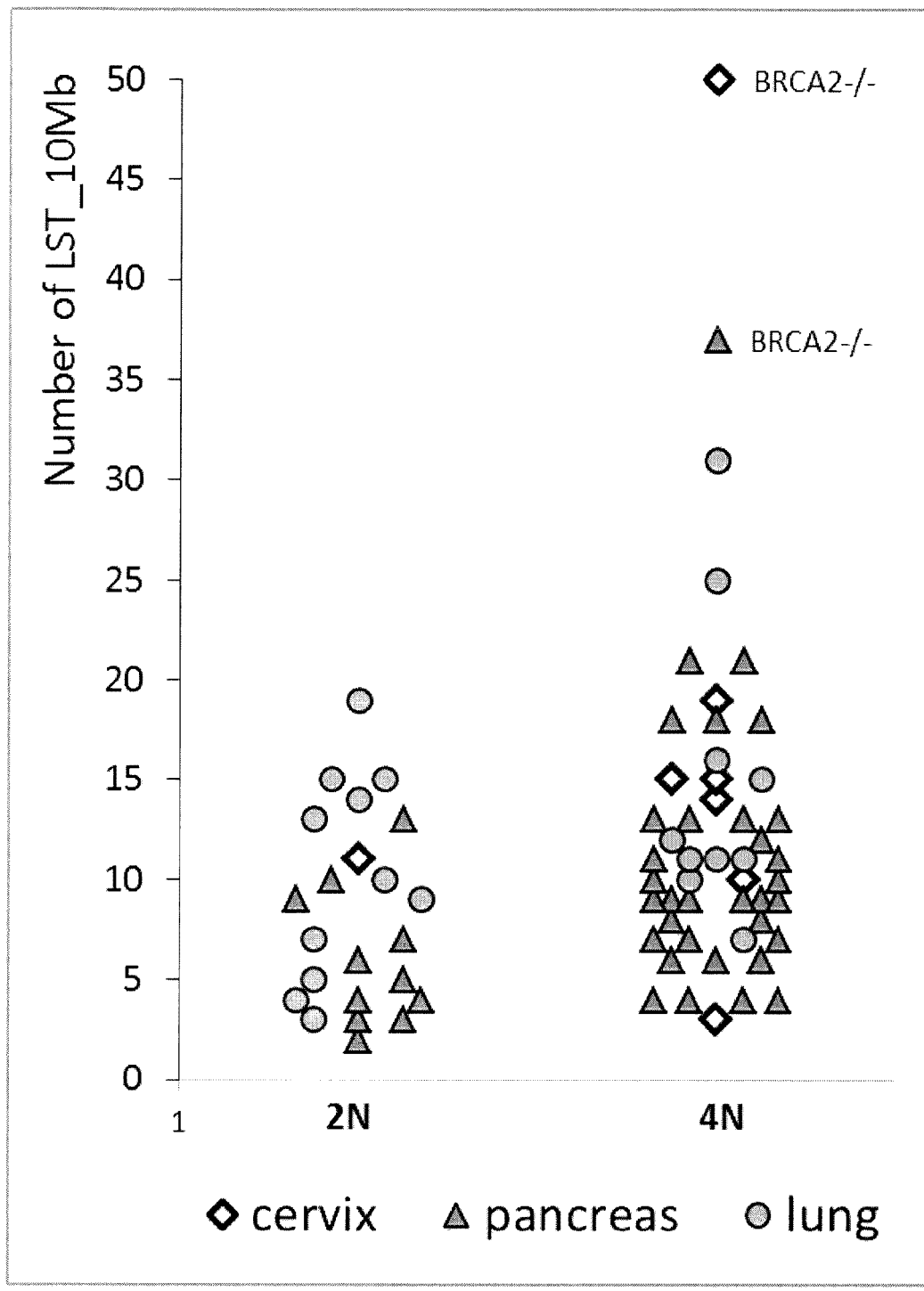

FIG. 7. LST_10 Mb in tumor cell lines.
Calculated ploidy is indicated (2N pseudo-diploid, 4N pseudo-tetraploid). Triangle: wild-type or unknown BRCA1/2 status; square: BRCA2 mutated cell lines.

EXAMPLES

Example 1

Materials and Methods

Patients and Tumors

A series of undifferentiated grade 3 BLCs was assembled from patients who had surgery at the Institut Curie. According to French regulations patients were informed of research and did not express opposition. High quality biological material was available at Institut Curie biobank for 85 tumor samples (some samples were described previously).[28-30] This series was enriched for tumors arisen in patients carrying deleterious BRCA1 mutations (35 tumors).

Immunohistochemistry

Immunostaining was performed on 4 μm tissue sections as described previously:[28,29] ER, PR and ERBB2 (Novocastra), EGFR and KRT8/18 (Zymed, Invitrogen), KRT5/6 (Dako) and KRT14 (Biogenex). Positivity for each marker was determined according to standardized guidelines.[31] Negativity was defined as total absence of staining for expression of ER and PR, and as less than 2+ staining for ERBB2.

The basal-like phenotype was defined according to morphological, phenotypic and/or molecular criteria including i) high grade (Elston-Ellis grading) and pushing margins, ii) triple-negative phenotype and expression of either KRT5/6/14/17 or EGFR assessed by immunohistochemistry.[32]

Methylation Status of BRCA1 Promoter

Methylation of the promoter of BRCA1 was assessed by methyl-specific PCR (MSP) after bisulfite conversion as described previously,[33] with minor modifications (primer sequences and protocols are available upon request).

BRCA1 Mutation Status

Pre-screen for mutations of the BRCA1 gene was performed using Enhanced Mismatch Mutation Analysis (EMMA, Fluigent[34]; EMMALYS software P/N: 5331254102). For abnormal EMMA profiles, the concerned BRCA1 exons were sequenced with dideoxynucleotides (BigDye Terminator V1.1, Applied Biosystems, Foster City, Calif.), according to standard protocols (primer sequences and protocols are available upon request). Sequences were examined with the Seqscape V2.5 (Applied Biosystems).

Analysis of Transcriptomic Data

Transcriptomic data was obtained on the Affymetrix U133plus2 platform in the Institut Curie according to the standard protocol. Normalization was performed with Brain-Array algorithm[35]. Unsupervised clustering was performed based on the intrinsic signature[36].

Processing the Genomic Profiles

Genomic profiling of 85 BLCs was performed using two platforms: Illumina (Illumina SNP HapMap 300K Duo, 33 cases) and Affymetrix (Affymetrix SNP Chip 6.0, 52 cases).

Illumina Platform:

Genomic profiling of the tumor samples was performed by a service provider (Integragen, Evry, France) on 300K Illumina SNP-arrays (Human Hap300-Duo). Raw data files were processed by BeadStudio 3.3 in standard settings using supporting data provided by Illumina (HumanHap300v2_A). Allele specific signals (X and Y in BeadStudio notation) were processed into Log R ratio and B allele frequency by tQN algorithm.[37]

Affymetrix Platform:

Hybridization was performed at Institut Curie on Affymetrix SNPChip6.0 array. Cell files were processed by Genotyping Console 3.0.2. Log 2Ratio and Allele Difference profiles resulted from Copy Number and LOH analysis performed with the reference model file HapMap270 (GenomeWideSNP_6.hapmap270.na29) provided by Affymetrix.

Quality Control:

20 SNP arrays were discarded due to: low hybridization quality (3 arrays); low tumor content and/or ambiguous profile interpretation (17 arrays).

Segmental Copy Number and Genotype Detection:

Both Illumina and Affymetrix SNP array data were mined using the GAP method described and validated previously: segmental copy numbers, allelic contents (major allele counts) and normal cell contamination were detected; segmentations were optimized with respect to the genomic status detected.[27]

Recognition of absolute copy number ranged from 0 to 8 copies with all segments exceeding 8-copy level been ascribed 8-copy status. Thus, 22 possible segmental genotypes were discriminated (copy number/major allele count): 1 copy A (or 1/1); 2 copies AA (2/2) and AB (2/1); 3 copies AAA (3/3), AAB (3/2); 4 copies AAAA (4/4), AAAB (4/3), AABB (4/2), etc. . . .

Chromosome Number:

Number of chromosomes was estimated by the sum of the copy numbers detected at the pericentric regions. The status of the pericentric region of each chromosome arm was defined by the corresponding juxta-centromeric segment when the latter contained 500 SNPs or more. When not measurable, missing values were substituted by the modal copy number of the considered chromosome arm (3.4±2.2 out of 41 chromosome arms per genome were substituted in the series). Chromosome counting procedure was validated by comparing estimated chromosome numbers versus available numbers from karyotype or SKY data for 25 breast cancer cell lines {lgcstandards-atcc.org/}. Error rate was less than 2 chromosomes per sample (1.58±2.3).

Breakpoint Counts:

Number of breakpoints in each genomic profile was estimated based on the resulting interpretable copy number profile and after filtering less than 50 SNPs variation. Small interstitial alterations were defined as <3 Mb alterations surrounded by the segments with identical status for genotype and copy number. They were removed when estimating total number of breakpoints. Large-scale State Transitions (LSTs) were calculated after smoothing and filtering of variation less than 3 Mb in size.

Compilation of Validation Sets

The validation series comprises 55 samples including TNBC from a cohort of young women with breast cancer (17 cases); BLCs with medullary features (8 cases) and one BLC arisen in a BRCA2 mutation carrier; BRCA1 BLCs from GEO GSE19177 (12 cases)[38]; basal-like tumors from GEO GSE32530 (4 cases)[39]; BRCA1 BLCs from Institut Bergonié (5 cases).

Basal-like cell lines with available SNP array profile comprised 17 cases (15 cases hybridized in Institute Curie and 2 cases were obtained from the Wellcome Trust Sanger Institute Cancer Genome Project web site.

Results

BRCA1 Status of Basal-Like Carcinomas (BLCs)

A series of 65 well characterized basal-like breast carcinomas included 23 tumors arisen in patients carrying deleterious BRCA1 mutations (herein called "BRCA1 BLCs") and 42 BLCs arisen in patients without evidence of familial predisposition of breast/ovarian cancer or tested negative for BRCA1/2 mutations (herein called "sporadic BLCs"). Sporadic BLCs were tested for the methylation of the BRCA1 promoter and nearly 25% were found positive (11 out of 41 tested, herein called "meBRCA1 BLCs"). No evidence of methylation in the remaining 31 cases was found. BRCA1 status was confirmed by the gene expression in 35 out of 36 tested cases with available transcriptomic data. BRCA1 and meBRCA1 BLCs comprise the group of tumors with proven BRCA1 inactivation (34 cases), which were further compared to the group of presumably non-BRCA1 BLCs (31 cases).

Near-Diploidy in BLCs has 75% Positive Predictive Value of BRCA1 Inactivation

In order to get insight into the specific genomic alterations of BLCs, genomic profiling was performed using SNP-arrays, which provide two complementary measurements: copy number variation and allelic imbalance. Genome Alteration Print (GAP) methodology for mining SNP arrays[27] allowed us to obtain the segmental genotype profiles (i.e. exact copy numbers and allelic contents: A, AB, AA, AAB, AAA, . . . ) for each sample. General genomic characteristics such as number of chromosomes, DNA index, number of chromosome breaks, and proportions of genome in each genomic state were inferred from the segmental genotype profiles.

Estimated chromosome counts per genome showed a bimodal distribution (FIG. 1, top panel) similar to those demonstrated for the genomes in various types of cancers[40]. Tumor genomes carrying less than 50 chromosomes and with the DNA index close to 1 were considered to have a ploidy of two and were thereafter called "near-diploid genomes" (23 cases). Following the hypothesis of the whole genome duplication during cancer progression explaining the second mode in chromosome distribution[40] tumor genomes carrying more than 50 chromosomes and DNA index higher than 1.2 were considered to have a ploidy of four and were thereafter called "over-diploid genomes" (42 cases).

Interestingly, the 23 near-diploid tumors almost consistently carried germline mutation or epigenetic inactivation of BRCA1 (20/23) in contrast to the over-diploid tumors, which were slightly enriched in non-BRCA1 BLCs (28/42) (FIG. 1, bottom pannel). Taking into account the fact that BRCA1 germline mutation is responsible for near 10% of basal-like carcinomas[41] positive predictive value of genomic near-diploid status was estimated to be 75%.

Large-Scale Chromosomal Rearrangements Discriminate BRCA1 and Non-BRCA1 Basal-Like Carcinomas Total number of breakpoints detected in the cancer genome characterizes the level of genomic instability. However, overall comparison of BRCA1 versus non-BRCA1 tumors did not show any significant difference (p-value=0.28). In the subgroup of 42 over-diploid BLCs, 14 BRCA1-inactivated tumors displayed elevated total number of breakpoints (range [57-224], 140.6±45.7), while 28 non-BRCA1 tumors showed significant heterogeneity (range [8-213], 101.2±50.6) and were enriched in the low values compared to BRCA1 tumors (p<0.017, Wilcoxon rank test). However, large overlap in the breakpoint numbers precluded accurate demarcation.

In order to get a robust and discriminative estimation of the genomic instability we evaluated the number of Large-scale State Transitions (LSTs) by calculating chromosomal breaks between adjacent regions of at least 10 Mb (comprising ~3000 SNPs in Affymetrix SNP6.0).

Number of LSTs in the subgroup of over-diploid tumors had a bimodal distribution with a clear gap between two modes (12.5±4.9 and 35.5±6.7) separating 18 non-BRCA1 BLCs from the mixture containing 14 BRCA1-inactivated tumors and 10 tumors with neither BRCA1 germline mutation nor BRCA1 promoter methylation (FIG. 2). In the subgroup of 23 near-diploid BLCs, which mainly contained BRCA1 tumors, LSTs had unimodal distribution (28.0±6.5) with two non-BRCA1 tumors within one standard deviation (24 and 28 LSTs) and one non-BRCA1 BLC below two standard deviations from the average (12 LSTs). Interestingly, all tumors with low LSTs had no evidence of BRCA1 inactivation and displayed either few chromosomal breaks and a high level of aneuploidy (3 samples) or firestorm-like alterations (16 samples).

To conclude, LSTs reflected well the overall genomic patterns of the tumors, contrary to the total number of breakpoints, and provided the discriminative values for BRCA1 status prediction.

A Two-Step Decision Rule Consistently Detects BRCA1 Inactivation in BLCs.

Based on the LSTs distributions described above, two thresholds for BRCAness prediction were applied, more than 15 LSTs per genome in the near-diploid cases and more than 20 LSTs in the over-diploid cases, predicting BRCAness with 100% sensitivity (p-value=4*10$^{-5}$, Fisher test).

Moreover, all "False Positive" cases (thereafter called "BRCA1-looking" BLCs) had similar high number of LSTs as the "True Positive" cases (with proven BRCA1-inactivated status), which actually questioned their false positive status and might evidence other mechanisms of homologous recombinaison defect including BRCA1 or BRCA2 mutations. Such mutations were searched in 28 sporadic BLCs with available material including 13 cases with the BRCA1-looking pattern. Deleterious BRCA1 mutations were found in six cases all belonging to BRCA1-looking tumors (p-value=0.02). Deleterious BRCA2 mutations were found in three cases all belonging to BRCA1-looking tumors. With these findings specificity reached 89% (p-value=1.4*10$^{-11}$, Fisher test) in the considered experimental set of BLCs (FIG. 3A).

A validation series of 55 BLC/TNBC was assembled, including 15 cases with BRCA1 germline mutations, 15 cases with BRCA1 promoter methylation, 1 case with a BRCA2 germline mutation, and 24 sporadic cases. SNP array data were processed using the same workflow. Prediction of the BRCA1 inactivation displayed sensitivity of 100% (all 30 BRCA1 inactivated cases were predicted to be BRCA1-looking) and specificity of 80% (11 cases were predicted to be BRCA1-looking with yet no evidence of BRCA1 inactivation) (FIG. 3B; p-value=1.7*10$^{-6}$, Fisher test). Noteworthy, the BRCA2 mutated tumor was near-diploid with a high LST number, thus clearly following a BRCA1-looking pattern.

Model Systems Supported the Discriminative Features Observed in the Primary Tumors A series of 17 basal-like cell lines was analyzed, including MDA-MB-436 and HCC1937 bearing BRCA1 mutations[42] and HCC38 with BRCA1 promoter methylation[43]. The obtained results followed the trend found in primary tumors: firstly the only near-diploid cell line found was the BRCA1 mutated MDA-MB-436; secondly among over-diploid cell lines, HCC1937 and HCC38 carried the highest number of large-scale chromosomal breaks, which is again consistent with their BRCA1-inactivated status. Nevertheless, and as expected considering cell line establishment and long term maintenance in culture, the cutoff separating non-BRCA1 cell lines was found shifted to 23 LSTs (FIG. 4). One cell line HCC1599 had LST number very close to BRCA1 inactivated cell lines, whereas not associated with BRCA1/2 mutation[44]. To clarify the BRCA1 function and more precisely the homologous recombination pathway, RAD51 foci were measured 8 hours after ionizing radiations in BLC cell lines. All cell lines without BRCA1 looking pattern had the expected RAD51 foci accumulation, whereas no foci were observed in cell lines with BRCA1 looking pattern, including HCC1599 (data not shown).

In conclusion, the inventors have shown that it is possible to predict tumor deficiency in the DNA homologous recombination (HR) pathway in a patient suffering from cancer, by quantifying the number of rearrangements in the genomic DNA of a tumor sample obtained from said patient, wherein the number of rearrangements corresponds to the number, per genome, of breakpoints resulting in segments of at least 10 megabases.

Similar results were obtained by using a cutoff value between 3 megabases and 20 megabases for the definition of Large Scale Transitions.

Example 2

Performance of LST Number Predicting BRCAness in all Types of Breast Carcinomas

The series of 426 breast tumors (invasive ductal carcinomas including HER2-positive tumors, luminal (eg expressing receptors for estrogen or progesterone), triple negative/basal-like breast carcinoma (eg expressing no hormone receptors and not overexpressing HER2) as well as rare subtypes such as medullary carcinomas or micropapillary carcinomas from Institut Curie) was considered. The series was enriched with BRCA1 and BRCA2 mutated tumors. The cut-offs on the LST number predicting BRCAness were inferred based on this series (Table 1). False Positive and True Positive Rates (FPR and TPR) show the quality of LST based predictor of BRCAness.

TABLE 1

Cut-offs for breast cancer BRCAness prediction based on the LST number

| LST_S Mb, S | Ploidy 2: (P = 68, N = 182) | | | Ploidy 4: (P = 53, N = 123) | | |
| --- | --- | --- | --- | --- | --- | --- |
|  | Cut-Off* | FPR | TPR | Cut-Off | FPR | TPR |
| 6 | 19 (17) | 0.04 | 0.99 | 32 (32) | 0.10 | 1 |
| 7 | 17 (15) | 0.05 | 0.99 | 29 (27) | 0.07 | 0.98 |
| 8 | 14 (14) | 0.06 | 1 | 26 (26) | 0.08 | 1 |
| 9 | 14 (11) | 0.04 | 0.99 | 25 (19) | 0.07 | 0.98 |
| 10 | 11 (11) | 0.07 | 1 | 22 (18) | 0.06 | 0.98 |

*Cut-offs correspond to max(TPR-FPR); cut-offs in parenthesis correspond to 100 sensitivity.
P: Number of positives, i.e. BRCA1/2 mutated tumors; N: Number of negatives, i.e. number of tumors with BRCA1/2 wild-type or status not available; TPR: True positive rate; FPR: False positive rate.

Example 3

The Number of LSTs is a Good Predictor of Response to Treatment

Two publically available data sets from clinical trial of Cisplatin treatment of patients with triple-negative breast tumors [GSE28330 GEO database][59] were processed and the number of LST_10 Mb was calculated for each tumor with good quality of measured profile. Genomic profiles were measured by two types of chip: Affymetrix Oncoscan 70K (Dataset 2) and Oncoscan 300K (Dataset 1). Information about mutational status of BRCA1/2 was available for some tumors. Response to treatment was measured by Miller-Payne score, where 4 and 5 were considered as "positive response", while scores <4 were considered as "no response" [59] Case by case and summary results are presented in Table 2 and Tables 3-5 (statistical comparisons were performed by the Fisher exact test). To conclude, (i) almost all known BRCA1/2 inactivated cases (17/18) and 15 tumors with wild-type or unknown BRCA1/2 status were classified as LST_high (Table 3); (ii) BRCA1/2 inactivation does not always mean response to Cisplatin (Table 4); (iii) LST_10 Mb is a better cisplatin response predictor than the BRCA1/2 status (Table 4-5).

TABLE 2

Individual results

| Data set | ID | Recognition Quality | BRCA1/2 | Miller-Payne response | LST | Response |
| --- | --- | --- | --- | --- | --- | --- |
| 1 | DFHCC_06.202_45R | good |  | 5 | High | Yes |
| 1 | DFHCC_06.202_15 | good | mut | 5 | High | Yes |
| 1 | DFHCC_06.202_41 | good |  | 5 | High | Yes |

TABLE 2-continued

Individual results

| Data set | ID | Recognition Quality | BRCA1/2 | Miller-Payne response | LST | Response |
|---|---|---|---|---|---|---|
| 1 | DFHCC_06.202_7 | good | mut | 5 | High | Yes |
| 1 | DFHCC_06.202_17 | good | | 5 | High | Yes |
| 2 | DFHCC_04.183_9T | good | non | 5 | High | Yes |
| 2 | DFHCC_04.183_18T | good | mut | 5 | High | Yes |
| 2 | DFHCC_04.183_3T | good | non | 5 | High | Yes |
| 2 | DFHCC_04.183_29T | good | non | 5 | High | Yes |
| 2 | DFHCC_04.183_5T | good | mut | 5 | High | Yes |
| 2 | DFHCC_04.183_17T | good | met | 5 | High | Yes |
| 1 | DFHCC_06.202_6 | good | met | 4 | High | Yes |
| 1 | DFHCC_06.202_48 | good | met | 4 | High | Yes |
| 2 | DFHCC_04.183_7T | good | met | 4 | High | Yes |
| 2 | DFHCC_04.183_8T | good | met | 4 | High | Yes |
| 1 | DFHCC_06.202_40 | good | | 4 | High | Yes |
| 2 | DFHCC_04.183_10T | good | non | 4 | High | Yes |
| 1 | DFHCC_06.202_3 | good | | 4 | High | Yes |
| 1 | DFHCC_06.202_27 | good | | 4 | Low | Yes |
| 1 | DFHCC_06.202_13 | good | met | 3 | High | No |
| 1 | DFHCC_06.202_5 | good | | 3 | Low | No |
| 1 | DFHCC_06.202_4 | good | met | 3 | High | No |
| 2 | DFHCC_04.183_23T | good | met | 3 | High | No |
| 2 | DFHCC_04.183_11T | good | non | 3 | High | No |
| 2 | DFHCC_04.183_25T | good | met | 3 | High | No |
| 2 | DFHCC_04.183_1T | good | met | 3 | High | No |
| 1 | DFHCC_06.202_37 | good | | 3 | Low | No |
| 1 | DFHCC_06.202_20 | good | mut | 2 | High | No |
| 1 | DFHCC_06.202_42 | good | mut | 2 | High | No |
| 1 | DFHCC_06.202_21 | good | | 2 | High | No |
| 2 | DFHCC_04.183_14T | good | non | 2 | High | No |
| 2 | DFHCC_04.183_24T | good | non | 2 | Low | No |
| 2 | DFHCC_04.183_22T | good | non | 2 | Low | No |
| 2 | DFHCC_04.183_28T | good | non | 2 | Low | No |
| 1 | DFHCC_06.202_24 | good | | 2 | Low | No |
| 1 | DFHCC_06.202_10 | good | | 1 | Low | No |
| 1 | DFHCC_06.202_32 | good | | 1 | Low | No |
| 1 | DFHCC_06.202_35 | good | | 1 | Low | No |
| 1 | DFHCC_06.202_46 | good | | 1 | Low | No |
| 2 | DFHCC_04.183_13T | good | non | 1 | Low | No |
| 1 | DFHCC_06.202_34 | good | | 1 | High | No |
| 1 | DFHCC_06.202_29 | good | | 1 | High | No |
| 1 | DFHCC_06.202_45L | good | | 1 | High | No |
| 2 | DFHCC_04.183_4T | good | non | 1 | High | No |
| 2 | DFHCC_04.183_12T | good | non | 1 | Low | No |
| 1 | DFHCC_06.202_18 | good | | 1 | Low | No |
| 1 | DFHCC_06.202_9 | good | | 1 | Low | No |
| 2 | DFHCC_04.183_16T | good | non | 1 | Low | No |
| 1 | DFHCC_06.202_14 | good | | 1 | Low | No |
| 2 | DFHCC_04.183_6T | good | | 1 | Low | No |
| 1 | DFHCC_06.202_28 | good | | 0 | Low | No |
| 2 | DFHCC_04.183_21T | good | non | 0 | High | No |
| 2 | DFHCC_04.183_27T | good | non | 0 | Low | No |
| 2 | DFHCC_04.183_26T | good | met | 0 | Low | No |
| 2 | DFHCC_04.183_15T | bad | met | 0 | | No |
| 2 | DFHCC_04.183_20T | bad | non | 2 | | No |
| 2 | DFHCC_06.202_33 | good | | NA | | |
| 2 | DFHCC_06.202_43 | good | | NA | | |
| 2 | DFHCC_06.202_50 | good | | NA | | |
| 2 | DFHCC_06.202_39 | bad | | 2 | | No |
| 2 | DFHCC_06.202_39 | bad | | 2 | | No |

TABLE 3

Summary of LST versus BRCA1/2

| ALL | LST_high | LST_low | |
|---|---|---|---|
| BRCA1/2 | 18 | 1 | p < 0.0001 |
| NON BRCA1/2 or NA | 15 | 20 | |

TABLE 4

Summary of BRCA1/2 versus Response

| ALL | Responders | Non Responders | |
|---|---|---|---|
| BRCA1/2 | 9 | 8 | p < 0.06 |
| NON BRCA1/2 or NA | 10 | 27 | |

TABLE 5

| Summary of LST versus Response | | | |
|---|---|---|---|
| ALL | LST_high | LST_low | |
| Non Responders | 15 | 20 | p < 0.0001 |
| Responders | 18 | 1 | |

Example 4

LST in Ovarian Carcinoma

Series of high grade ovarian carcinoma from Institut Curie were profiled by SNP arrays (Affymetrix CytoScanHD). All patients were treated by chemotherapies including platinum salts. Tumor genomes were annotated as LST_high (50 cases) and LST_low (20 cases) based on the LST_6 Mb with the cutoffs 19 and 32 LSTs for near-diploid and near-tetraploid tumors respectively. Comparison of Overall Survival and Event Free Survival showed better outcome for patients with LST_high tumors, which indicates better response to treatment (FIGS. 5-6).

Example 5

LST in Tumor Cell Lines

Series of tumor cell lines with known BRCA status and with available SNP-array data were analyzed. LST_10 Mb was calculated and samples with high LST were linked to BRCA2 inactivation in cervix and pancreatic carcinoma cell lines. Two lung cell lines without known BRCA1/2 mutations have a high level of LST, presumably due to BRCA1 methylation described in this disease [60] (FIG. 7). This validation of the method in tumor cell lines of various origins and state of differentiation indicates that LST measurement and prediction of the BRCAness can be applied in all types of tumors.

REFERENCES

1. Rakha E A, Reis-Filho J S, Ellis I O: Basal-like breast cancer: a critical review. J Clin Oncol 26:2568-81, 2008
2. Dawson S J, Provenzano E, Caldas C: Triple negative breast cancers: clinical and prognostic implications. Eur J Cancer 45 Suppl 1:27-40, 2009
3. Foulkes W D, Stefansson I M, Chappuis P O, et al: Germline BRCA1 mutations and a basal epithelial phenotype in breast cancer. J Natl Cancer Inst 95:1482-5, 2003
4. Bergamaschi A, Kim Y H, Wang P, et al: Distinct patterns of DNA copy number alteration are associated with different clinicopathological features and gene-expression subtypes of breast cancer. Genes Chromosomes Cancer 45:1033-40, 2006
5. Melchor L, Honrado E, Garcia M J, et al: Distinct genomic aberration patterns are found in familial breast cancer associated with different immunohistochemical subtypes. Oncogene 27:3165-75, 2008
6. Natrajan R, Weigelt B, Mackay A, et al: An integrative genomic and transcriptomic analysis reveals molecular pathways and networks regulated by copy number aberrations in basal-like, HER2 and luminal cancers. Breast Cancer Res Treat, 2009
7. Gudmundsdottir K, Ashworth A: The roles of BRCA1 and BRCA2 and associated proteins in the maintenance of genomic stability. Oncogene 25:5864-74, 2006
8. Roy R, Chun J, Powell S N: BRCA1 and BRCA2: different roles in a common pathway of genome protection. Nat Rev Cancer 12:68-78, 2012
9. Turner N, Tutt A, Ashworth A: Hallmarks of 'BRCAness' in sporadic cancers. Nat Rev Cancer 4:814-9, 2004
10. Chin S F, Teschendorff A E, Marioni J C, et al: High-resolution aCGH and expression profiling identifies a novel genomic subtype of ER negative breast cancer. Genome Biol 8:R215, 2007
11. Stefansson O A, Jonasson J G, Johannsson O T, et al: Genomic profiling of breast tumours in relation to BRCA abnormalities and phenotypes. Breast Cancer Res 11:R47, 2009
12. Joosse S A, Brandwijk K I, Mulder L, et al: Genomic signature of BRCA1 deficiency in sporadic basal-like breast tumors. Genes Chromosomes Cancer 50:71-81, 2011
13. Farmer H, McCabe N, Lord C J, et al: Targeting the DNA repair defect in BRCA mutant cells as a therapeutic strategy. Nature 434:917-21, 2005
14. Bryant H E, Schultz N, Thomas H D, et al: Specific killing of BRCA2-deficient tumours with inhibitors of poly(ADP-ribose) polymerase. Nature 434:913-7, 2005
15. Fong P C, Boss D S, Yap T A, et al: Inhibition of poly(ADP-ribose) polymerase in tumors from BRCA mutation carriers. N Engl J Med 361:123-34, 2009
16. Vollebergh M A, Jonkers J, Linn S C: Genomic instability in breast and ovarian cancers: translation into clinical predictive biomarkers. Cell Mol Life Sci 69:223-45, 2012
17. Focken T, Steinemann D, Skawran B, et al: Human BRCA1-Associated Breast Cancer: No Increase in Numerical Chromosomal Instability Compared to Sporadic Tumors. Cytogenet Genome Res 135:84-92, 2011
18. Johannsdottir H K, Jonsson G, Johannesdottir G, et al: Chromosome 5 imbalance mapping in breast tumors from BRCA1 and BRCA2 mutation carriers and sporadic breast tumors. Int J Cancer 119:1052-60, 2006
19. Tirkkonen M, Johannsson O, Agnarsson B A, et al: Distinct somatic genetic changes associated with tumor progression in carriers of BRCA1 and BRCA2 germ-line mutations. Cancer Res 57:1222-7, 1997
20. Melchor L, Alvarez S, Honrado E, et al: The accumulation of specific amplifications characterizes two different genomic pathways of evolution of familial breast tumors. Clin Cancer Res 11:8577-84, 2005
21. Wessels L F, van Welsem T, Hart A A, et al: Molecular classification of breast carcinomas by comparative genomic hybridization: a specific somatic genetic profile for BRCA1 tumors. Cancer Res 62:7110-7, 2002
22. Waddell N, Arnold J, Cocciardi S, et al: Subtypes of familial breast tumours revealed by expression and copy number profiling. Breast Cancer Res Treat, 2009
23. Jonsson G, Staaf J, Vallon-Christersson J, et al: Genomic subtypes of breast cancer identified by array-comparative genomic hybridization display distinct molecular and clinical characteristics. Breast Cancer Res 12:R42, 2010
24. Joosse S A, van Beers E H, Tielen I H, et al: Prediction of BRCA1-association in hereditary non-BRCA1/2 breast carcinomas with array-CGH. Breast Cancer Res Treat 116:479-89, 2009
25. Lips E H, Mulder L, Hannemann J, et al: Indicators of homologous recombination deficiency in breast cancer and association with response to neoadjuvant chemotherapy. Ann Oncol 22:870-6, 2011
26. Vollebergh M A, Lips E H, Nederlof P M, et al: An aCGH classifier derived from BRCA1-mutated breast cancer and benefit of high-dose platinum-based chemotherapy in HER2-negative breast cancer patients. Ann Oncol 22:1561-70, 2011
27. Popova T, Manie E, Stoppa-Lyonnet D, et al: Genome Alteration Print (GAP): a tool to visualize and mine complex cancer genomic profiles obtained by SNP arrays. Genome Biol 10:R128, 2009
28. Manie E, Vincent-Salomon A, Lehmann-Che J, et al: High frequency of TP53 mutation in BRCA1 and sporadic basal-like carcinomas but not in BRCA1 luminal breast tumors. Cancer Res 69:663-71, 2009
29. Vincent-Salomon A, Gruel N, Lucchesi C, et al: Identification of typical medullary breast carcinoma as a genomic sub-group of basal-like carcinomas, a heterogeneous new molecular entity. Breast Cancer Res 9:R24, 2007
30. Marty B, Maire V, Gravier E, et al: Frequent PTEN genomic alterations and activated phosphatidylinositol 3-kinase pathway in basal-like breast cancer cells. Breast Cancer Res 10:R101, 2008
31. Azoulay S, Lae M, Freneaux P, et al: KIT is highly expressed in adenoid cystic carcinoma of the breast, a basal-like carcinoma associated with a favorable outcome. Mod Pathol 18:1623-31, 2005
32. Nielsen T O, Hsu F D, Jensen K, et al: Immunohistochemical and clinical characterization of the basal-like subtype of invasive breast carcinoma. Clin Cancer Res 10:5367-74, 2004
33. Esteller M, Silva J M, Dominguez G, et al: Promoter hypermethylation and BRCA1 inactivation in sporadic breast and ovarian tumors. Natl Cancer Inst 92:564-9, 2000
34. Houdayer C, Moncoutier V, Champ J, et al: Enhanced mismatch mutation analysis: simultaneous detection of point mutations and large scale rearrangements by capillary electrophoresis, application to BRCA1 and BRCA2. Methods Mol Biol 653:147-80, 2010
35. Dai M, Wang P, Boyd A D, et al: Evolving gene/transcript definitions significantly alter the interpretation of GeneChip data. Nucleic Acids Res 33:e175, 2005
36. Sorlie T, Tibshirani R, Parker J, et al: Repeated observation of breast tumor subtypes in independent gene expression data sets. Proc Natl Acad Sci USA 100:8418-23, 2003
37. Staaf J, Vallon-Christersson J, Lindgren D, et al: Normalization of Illumina Infinium whole-genome SNP data improves copy number estimates and allelic intensity ratios. BMC Bioinformatics 9:409, 2008
38. Waddell N, Arnold J, Cocciardi S, et al: Subtypes of familial breast tumours revealed by expression and copy number profiling. Breast Cancer Res Treat 123:661-77, 2010
39. DeRose Y S, Wang G, Lin Y C, et al: Tumor grafts derived from women with breast cancer authentically reflect tumor pathology, growth, metastasis and disease outcomes. Nat Med 17:1514-20, 2011
40. Storchova Z, Kuffer C: The consequences of tetraploidy and aneuploidy. J Cell Sci 121:3859-66, 2008
41. Young S R, Pilarski R T, Donenberg T, et al: The prevalence of BRCA1 mutations among young women with triple-negative breast cancer. BMC Cancer 9:86, 2009
42. Elstrodt F, Hollestelle A, Nagel J H, et al: BRCA1 mutation analysis of 41 human breast cancer cell lines reveals three new deleterious mutants. Cancer Res 66:41-5, 2006
43. Xu J, Huo D, Chen Y, et al: CpG island methylation affects accessibility of the proximal BRCA1 promoter to transcription factors. Breast Cancer Res Treat 120:593-601, 2010
44. Sjoblom T, Jones S, Wood L D, et al: The consensus coding sequences of human breast and colorectal cancers. Science 314:268-74, 2006
45. Garcia A I, Buisson M, Bertrand P, et al: Down-regulation of BRCA1 expression by miR-146a and miR-146b-5p in triple negative sporadic breast cancers. EMBO Mol Med 3:279-90, 2011
46. Moskwa P, Buffa F M, Pan Y, et al: miR-182-mediated downregulation of BRCA1 impacts DNA repair and sensitivity to PARP inhibitors. Mol Cell 41:210-20, 2011
47. Plo I, Laulier C, Gauthier L, et al: AKT1 inhibits homologous recombination by inducing cytoplasmic retention of BRCA1 and RAD51. Cancer Res 68:9404-12, 2008
48. Van Loo P, Nordgard S H, Lingjaerde O C, et al: Allele-specific copy number analysis of tumors. Proc Natl Acad Sci USA 107:16910-5, 2010
49. Pujana M A, Han J D, Starita L M, et al: Network modeling links breast cancer susceptibility and centrosome dysfunction. Nat Genet 39:1338-49, 2007
50. Xu X, Weaver Z, Linke S P, et al: Centrosome amplification and a defective G2-M cell cycle checkpoint induce genetic instability in BRCA1 exon 11 isoform-deficient cells. Mol Cell 3:389-95, 1999
51. Brodie K M, Henderson B R: Characterization of BRCA1 centrosome targeting, dynamics and function: A role for the nuclear export signal, CRM1 and Aurora A kinase. J Biol Chem, 2012
52. Kais Z, Parvin J D: Regulation of centrosomes by the BRCA1-dependent ubiquitin ligase. Cancer Biol Ther 7:1540-3, 2008
53. Moller P, Hagen A I, Apold J, et al: Genetic epidemiology of BRCA mutations—family history detects less than 50% of the mutation carriers. Eur J Cancer 43:1713-7, 2007
54. O'Shaughnessy J, Telli M, Swain S, et al: Phase 3 Study of Iniparib (I) Plus Gemcitabine (G) and Carboplatin (C) in Metastatic Triple-negative Breast Cancer (mTNBC)—Results of an Exploratory Analysis by Prior Therapy European Journal of Cancer 47:S338, 2011
55. Miki Y, Swensen J, Shattuck-Eidens D, Futreal P A, Harshman K, Tavtigian S, Liu Q, Cochran C, Bennett L M, Ding W and et al. (1994). A strong candidate for the breast and ovarian cancer susceptibility gene BRCA1. Science, 266, 66-71.
56. Wooster R, Bignell G, Lancaster J, Swift S, Seal S, Mangion J, Collins N, Gregory S, Gumbs C and Micklem G. (1995). Identification of the breast cancer susceptibility gene BRCA2. Nature, 378, 789-92.
57. Esteller M, Silva J M, Dominguez G, Bonilla F, Matias-Guiu X, Lerma E, Bussaglia E, Prat J, Harkes I C, Repasky E A, Gabrielson E, Schutte M, Baylin S B and Herman J G. (2000). Promoter hypermethylation and BRCA1 inactivation in sporadic breast and ovarian tumors. J Natl Cancer Inst, 92, 564-9.
58. Stephens P J, McBride D J, Lin M L, Varela I, Pleasance E D, Simpson J T, Stebbings L A, Leroy C, Edkins S, Mudie L J, Greenman C D, Jia M, Latimer C, Teague J W, Lau K W, Burton J, Quail M A, Swerdlow H, Churcher C, Natrajan R, Sieuwerts A M, Martens J W, Silver D P, Langerod A, Russnes H E, Foekens J A, Reis-Filho J S, van't Veer L, Richardson A L, Borresen-Dale A L, Campbell P J, Futreal P A and Stratton M R. (2009). Complex landscapes of somatic rearrangement in human breast cancer genomes. Nature, 462, 1005-10.

59. Birkbak, N. J., Wang, Z. C., Kim, J. Y., Eklund, A. C., Li, Q., Tian, R., Bowman-Colin, C., Li, Y., Greene-Colozzi, A., Iglehart, J. D., et al. (2012). Telomeric allelic imbalance indicates defective DNA repair and sensitivity to DNA-damaging agents. Cancer Discovery 2, 366-375.

60. Lee, M.-N., Tseng, R.-C., Hsu, H.-S., Chen, J.-Y., Tzao, C., Ho, W. L., and Wang, Y.-C. (2007). Epigenetic inactivation of the chromosomal stability control genes BRCA1, BRCA2, and XRCC5 in non-small cell lung cancer. Clin. Cancer Res. 13, 832-838.

The invention claimed is:

1. A method for treating cancer, the method comprising administering a therapeutically effective amount of a PARP inhibitor and/or an alkylating agent to a human patient identified as having, in a tumor sample obtained from the patient, a number, per genome, of large scale transitions (LSTs) greater than a threshold number of LSTs, wherein (a) an LST is a breakpoint between two genomic regions of different copy number, each such genomic region being at least 6 megabases long; and (b) the threshold number of LSTs is any integer equal to or greater than 11.

2. The method of claim 1, wherein said PARP inhibitor and/or alkylating agent is selected from the group consisting of iniparib, olaparib, rucaparib, CEP 9722, MK 4827, BMN-673, 3-aminobenzamide, platinum complexes, chlormethine, chlorambucil, melphalan, cyclophosphamide, ifosfamide, estramustine, carmustine, lomustine, fotemustine, streptozocin, busulfan, pipobroman, procarbazine, dacarbazine, thiotepa and temozolomide.

3. The method of claim 1, wherein the cancer is selected from breast cancer, ovary cancer, pancreas cancer, head and neck carcinoma and melanoma.

4. The method of claim 1, wherein the cancer is breast cancer.

5. The method of claim 1, wherein the cancer is basal-like breast cancer.

6. The method of claim 1, wherein the patient is identified by detecting, in the tumor sample, the number of LSTs per genome.

7. The method of claim 6, wherein the number of LSTs per genome is detected by detecting copy number for at least 500 Single Nucleotide Polymorphism (SNP) loci.

8. The method of claim 6, wherein the number of LSTs per genome is detected by detecting copy number for at least 3,000 Single Nucleotide Polymorphism (SNP) loci.

9. The method of claim 6, wherein the number of LSTs per genome is detected by comparative genomic hybridization (CGH) array, Single Nucleotide Polymorphism (SNP) array, or sequencing of polymorphic loci.

10. The method of claim 1, wherein an LST is a breakpoint between two genomic regions of different copy number, each such genomic region being at least 7 megabases long.

11. The method of claim 1, wherein an LST is a breakpoint between two genomic regions of different copy number, each such genomic region being at least 8 megabases long.

12. The method of claim 1, wherein an LST is a breakpoint between two genomic regions of different copy number, each such genomic region being at least 9 megabases long.

13. The method of claim 1, wherein an LST is a breakpoint between two genomic regions of different copy number, each such genomic region being at least 10 megabases long.

14. The method of claim 1, wherein an LST is a breakpoint between two genomic regions of different copy number, each such genomic region being at least 11 megabases long.

15. The method of claim 1, wherein an LST is a breakpoint between two genomic regions of different copy number, each such genomic region being at least 12 megabases long.

16. The method of claim 1, wherein an LST is a breakpoint between two genomic regions of different copy number, each such genomic region being at least 13 megabases long.

17. The method of claim 1, wherein an LST is a breakpoint between two genomic regions of different copy number, each such genomic region being at least 14 megabases long.

18. The method of claim 1, wherein an LST is a breakpoint between two genomic regions of different copy number, each such genomic region being at least 15 megabases long.

19. The method of claim 1, the threshold number of LSTs is any integer equal to or greater than 12.

20. The method of claim 1, the threshold number of LSTs is any integer equal to or greater than 13.

21. The method of claim 1, the threshold number of LSTs is any integer equal to or greater than 14.

22. The method of claim 1, the threshold number of LSTs is any integer equal to or greater than 15.

23. The method of claim 1, the threshold number of LSTs is any integer equal to or greater than 16.

24. The method of claim 1, the threshold number of LSTs is any integer equal to or greater than 17.

25. The method of claim 1, the threshold number of LSTs is any integer equal to or greater than 18.

26. The method of claim 1, the threshold number of LSTs is any integer equal to or greater than 19.

27. The method of claim 1, the threshold number of LSTs is any integer equal to or greater than 20.

28. A method for treating cancer, the method comprising administering a therapeutically effective amount of a PARP inhibitor and/or an alkylating agent to a patient identified as having, in a tumor sample obtained from the patient, more than 12 large scale transitions (LSTs) per genome, an LST being a breakpoint between two genomic regions of different copy number, each such genomic region being at least 6 megabases long.

* * * * *

UNITED STATES PATENT AND TRADEMARK OFFICE
CERTIFICATE OF CORRECTION

| | |
|---|---|
| PATENT NO. | : 11,091,808 B2 |
| APPLICATION NO. | : 14/402254 |
| DATED | : August 17, 2021 |
| INVENTOR(S) | : M. Stern, E. Manie and T. Popova |

It is certified that error appears in the above-identified patent and that said Letters Patent is hereby corrected as shown below:

On the Title Page

Item [86], the § 371 (c)(1), (2) date should read November 19, 2014.

Signed and Sealed this
First Day of November, 2022

Katherine Kelly Vidal
*Director of the United States Patent and Trademark Office*